(12) United States Patent
Chun

(10) Patent No.: US 8,092,997 B2
(45) Date of Patent: Jan. 10, 2012

(54) PROCESSES USING DUAL SPECIFICITY OLIGONUCLEOTIDE AND DUAL SPECIFICITY OLIGONUCLEOTIDE

(75) Inventor: Jong-Yoon Chun, Seoul (KR)

(73) Assignee: Seegene, Inc., Seoul (KR)

( * ) Notice: Subject to any disclaimer, the term of this patent is extended or adjusted under 35 U.S.C. 154(b) by 728 days.

(21) Appl. No.: 11/817,838

(22) PCT Filed: Mar. 3, 2006

(86) PCT No.: PCT/KR2006/000746
§ 371 (c)(1),
(2), (4) Date: Aug. 21, 2008

(87) PCT Pub. No.: WO2006/095981
PCT Pub. Date: Sep. 14, 2006

(65) Prior Publication Data
US 2008/0305478 A1    Dec. 11, 2008

(30) Foreign Application Priority Data

Mar. 5, 2005 (KR) .................. 10-2005-0018419
Apr. 26, 2005 (KR) ................ PCT/KR2005/001206

(51) Int. Cl.
*C12Q 1/68* (2006.01)
(52) U.S. Cl. ....................................................... 435/6.1
(58) Field of Classification Search ............ None
See application file for complete search history.

(56) References Cited

U.S. PATENT DOCUMENTS 6,197,556 B1 * 3/2001 Ulanovsky et al. .......... 435/91.2
2003/0170711 A1   9/2003 Brown et al.

FOREIGN PATENT DOCUMENTS

WO   WO 03/050305 A1   6/2003
WO   WO 03050305 A1 *  6/2003

OTHER PUBLICATIONS

Bartl et al. (Biotechniques. Feb. 1994;16(2):246-8, 250).*
Hwang, et al., "Annealing control primer system for improving specificity of PCR amplification," Biotechniques, 35(6), pp. 1180-1184, (Dec. 2003).
Kim, et al., "Annealing control primer system for identification of differentially expressed genes on agarose gels," Biotechniques, 36(3), pp. 424-434, (Mar. 2004).
Hwang, et al., "Identification of differentially regulated genes in bovine blastocysts using an annealing control primer system," Molecular Reproduction and Development, 69(1), pp. 43-51, (Sep. 2004).
International Search Report based on International Application No. PCT/KR2006/000746, (Jun. 14, 2006).

* cited by examiner

*Primary Examiner* — Christopher M. Babic
(74) *Attorney, Agent, or Firm* — Saul Ewing LLP; Gianna Julian-Arnold

(57) ABSTRACT

The present invention relates to various processes by a template-dependent extension reaction using a dual specificity oligonucleotide and a dual specificity oligonucleotide composed of three different Tm portions therefor. Demonstrated in the present invention are the features of the dual specificity oligonucleotide, which are high hybridization specificity and mismatch tolerance.

36 Claims, 14 Drawing Sheets

FIG. 1A

High Hybridization Specificity of Dual Specificity Oligonucleotide (a) No Extension
   Extension does not occur
   when the 5'-end portion, yet not the 3'-end portion, is annealed to the template

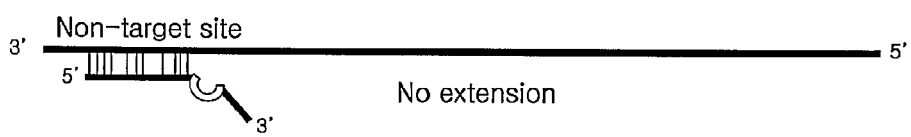

(b) No Annealing
   Annealing does not occur
   when the 3'-end portion, yet not the 5'-end portion, has a sequence complementary
   to the non-target site

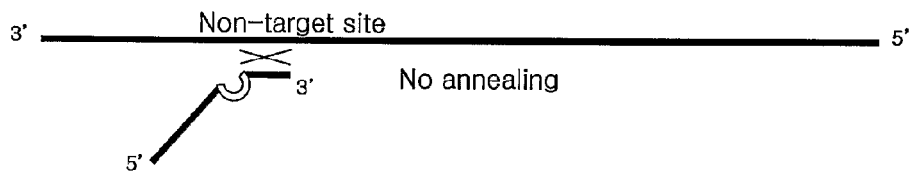

(c) Extension
   Both 5'- and 3'-end portions are annealed to the target sequence
   and hence successful extension.

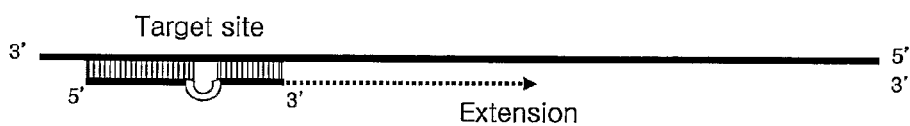

FIG. 1B

Mismatch Tolerance of Dual Specificity Oligonucleotide (a) Extension

Mismatch at the 5'-end portion is tolerated as both 5'- and 3'-end portions are annealed to the template

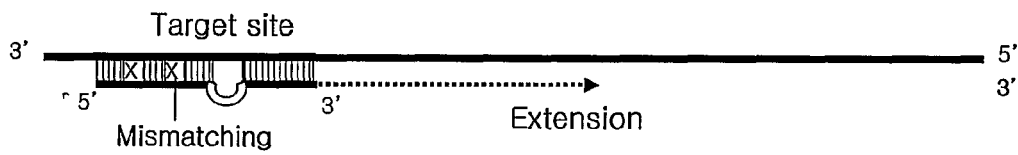

(b) Extension

Mismatch at the 3'-end portion is tolerated as both 5'- and 3'-end portions are annealed to the template

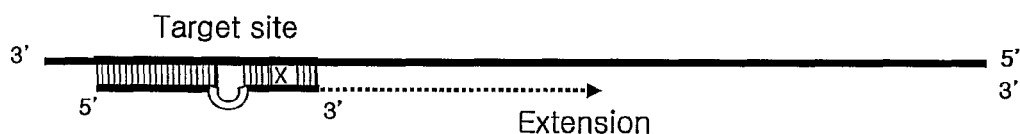

(c) Extension

Mismatches at the 5'- and 3'-end portions are tolerated as both 5'- and 3'-end portions are annealed to the template.

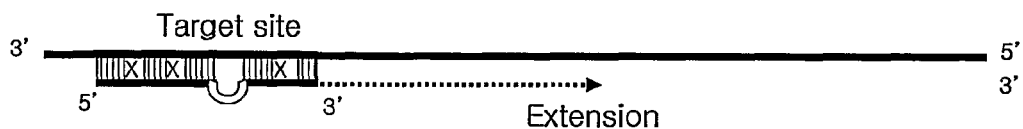

FIG. 4
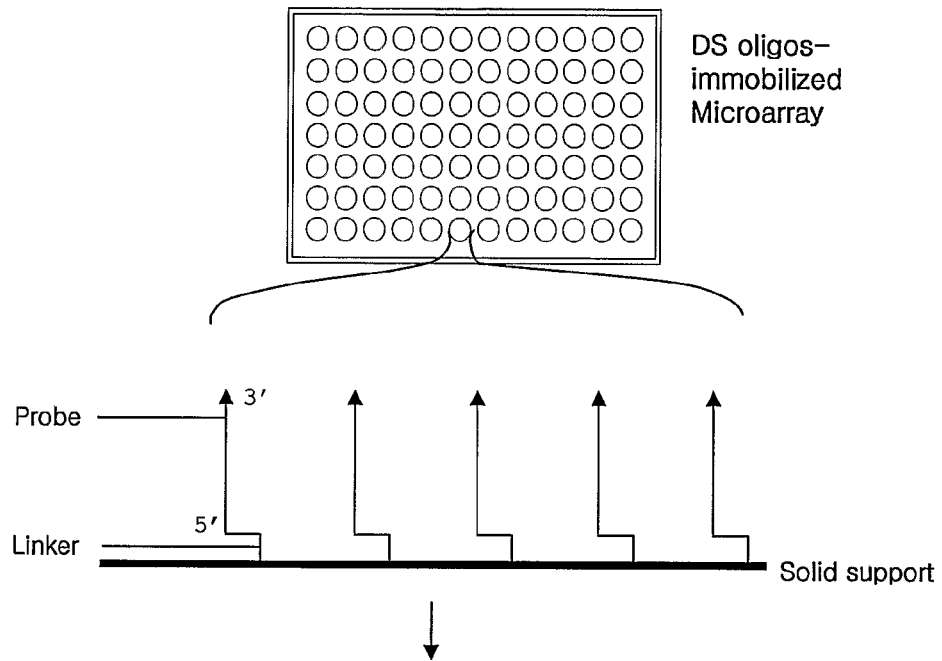
1st cycle : Template nucleic acids hybridize to target oligonucleotide probes, followed by complementary extension
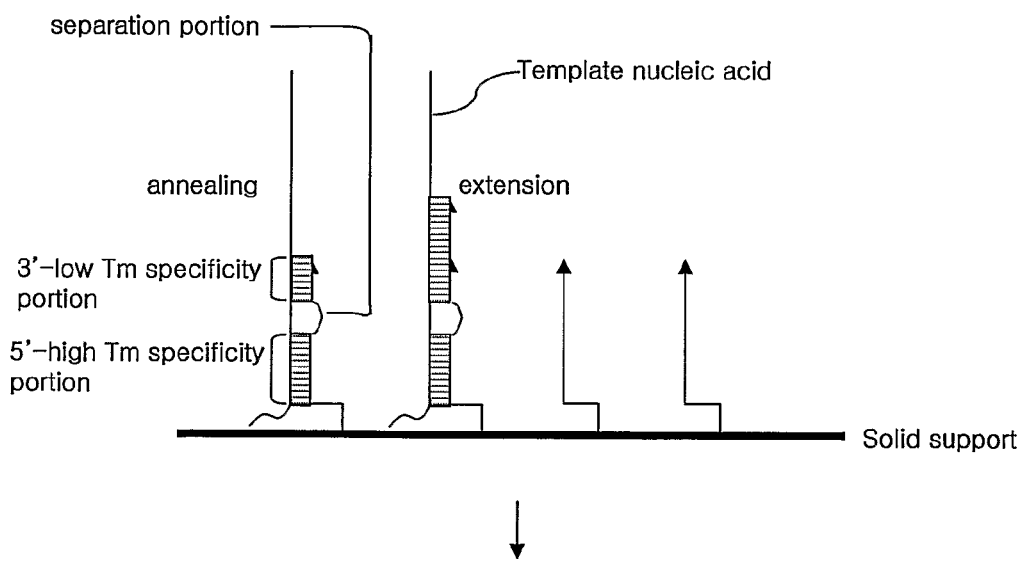

FIG. 4 (continued)
2nd cycle : The un-hybridized target oligonucleotide probes are hybridized by template nucleic acids, followed by complementary extension.
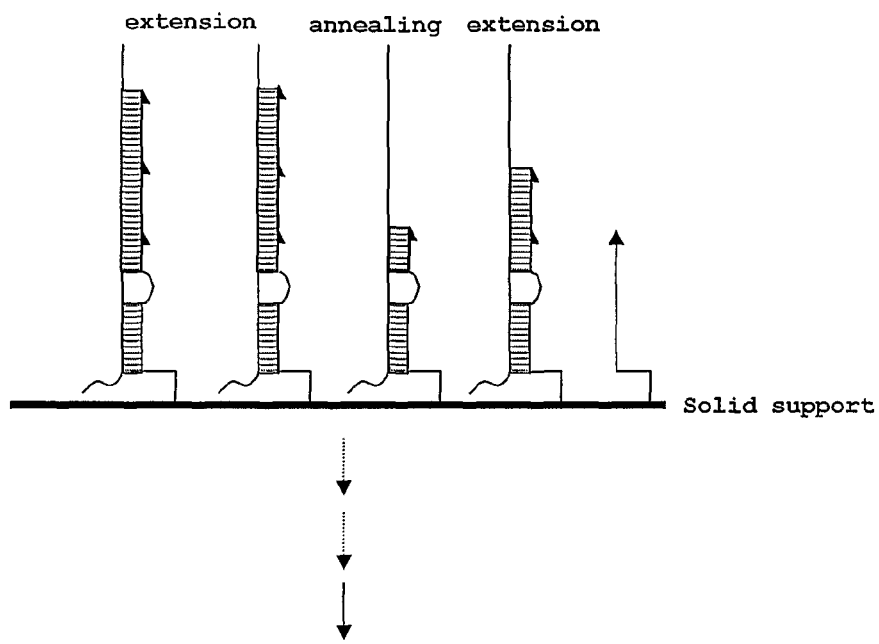
The cycle is repeated until all or most target oligonucleotide probes are hybridized with template nucleic acids.
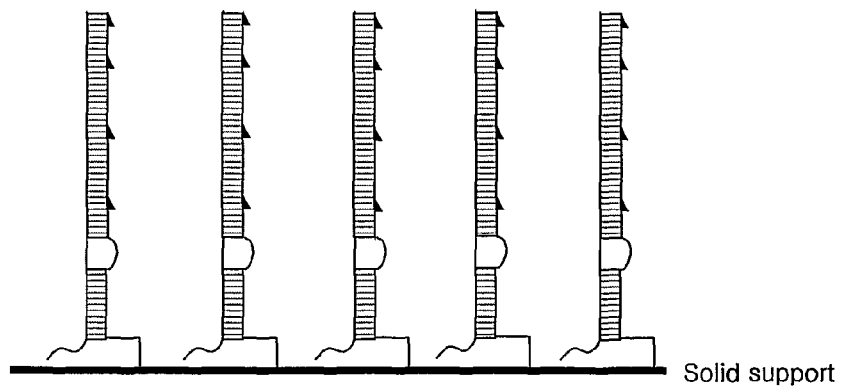

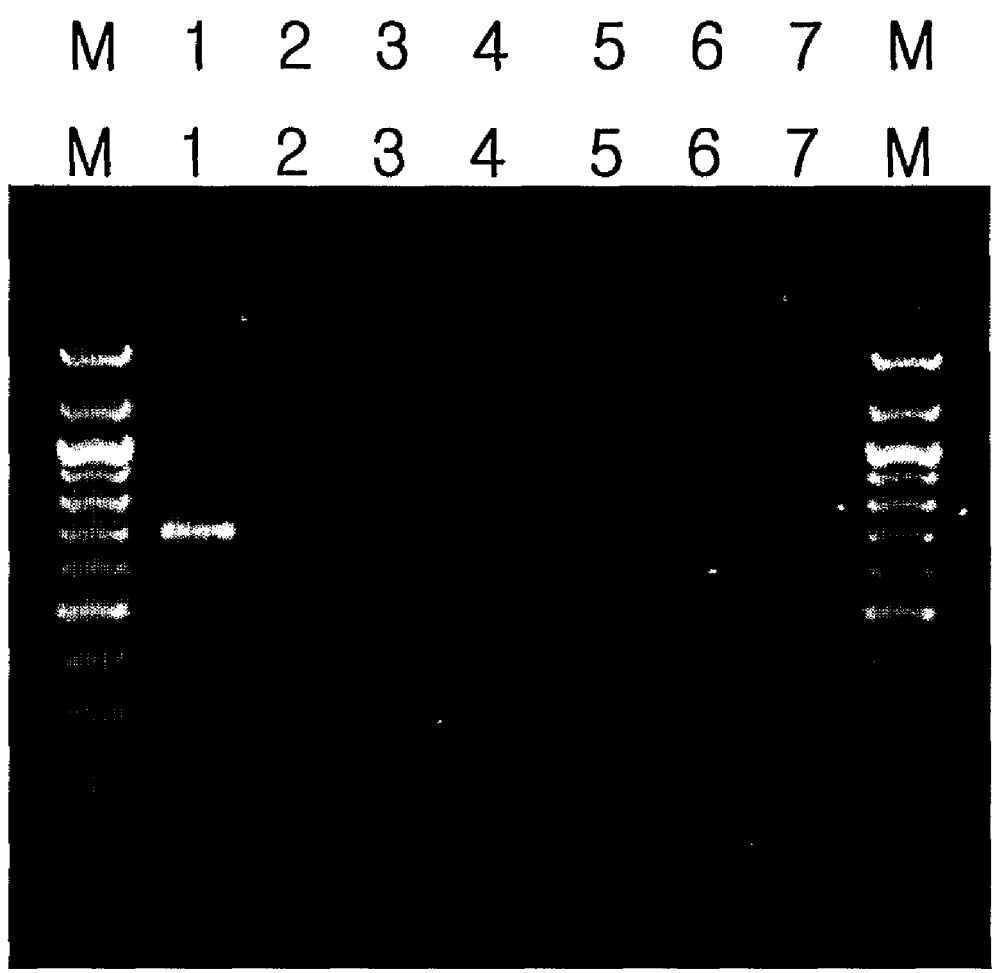

FIG. 7A

```
Psx1    580 GTAAGGAGGGATCTTGCACGATGGATGGGTGTGGATGAATGTGATGTGCAGAATTGGT......
Psx2    580 GTAAGGAGGGATCTTGCACGATGGATGGGTGTGGATGAATCTGATGTGCAGGAGTGGT......

⎧ Psx1-5'-40: 5'-TCTTGCACGATGGATGGGTGTGGATGAATGTGA-3'
5'      ⎪ Psx2-5'-40: 5'-TCTTGCACGATGGATGGGTGTGGATGAATCTGA-3'
primers ⎨ Psx1-5'-41: 5'-TCTTGCACGATGGATGGGTGTTTTGAATGTGA-3'
        ⎩ Psx2-5'-41: 5'-TCTTGCACGATGGATGGGTGTTTTGAATCTGA-3'
```

PROCESSES USING DUAL SPECIFICITY OLIGONUCLEOTIDE AND DUAL SPECIFICITY OLIGONUCLEOTIDE

RELATED APPLICATIONS

This application is a National Stage of PCT/KR2006/000746, filed Mar. 3, 2006, which claims the benefit of Korean Patent Application No. 10-2005-0018419, filed Mar. 5, 2005, and PCT/KR2005/001206, filed Apr. 26, 2005, all of which are herein incorporated by reference in their entireties.

BACKGROUND OF THE INVENTION

1. Field of the Invention

The present invention relates to various processes using a dual specificity oligonucleotide and a dual specificity oligonucleotide therefor. More particularly, the present invention relates to various processes by a template-dependent extension reaction using a dual specificity oligonucleotide and a dual specificity oligonucleotide therefor.

2. Description of the Related Art

Nucleic acid amplification is a pivotal process for a wide variety of methods in molecular biology, such that various amplification methods have been proposed. For example, Miller, H. I. et al. (WO 89/06700) amplified a nucleic acid sequence based on the hybridization of a promoter/primer sequence to a target single-stranded DNA ("ssDNA") followed by transcription of many RNA copies of the sequence. Other known nucleic acid amplification procedures include transcription-based amplification systems (Kwoh, D. et al., *Proc. Natl. Acad. Sci. U.S.A.,* 86:1173 (1989); and Gingeras T. R. et al., WO 88/10315).

The most predominant process for nucleic acid amplification known as polymerase chain reaction (hereinafter referred to as "PCR"), is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) *Science* 230, 1350-1354). The oligonucleotide primers used in PCR are designed to anneal to opposite strands of the DNA template. The primers are extended by DNA polymerase, from which the product of one primer can serve as the template strand for the other primer in subsequential reactions. The PCR amplification process results in the exponential increase of discrete DNA fragments whose length is defined by the 5' ends of the oligonucleotide primers.

The success in nucleic acid amplifications, in particular PCR amplification, relies on the specificity with which a primer anneals only to its target (and not non-target) sequences; therefore, it is important to optimize this molecular interaction. Whether a primer can anneal only to its perfect complement or also to sequences that have one or more mismatches depends critically upon the annealing temperature. In general, higher annealing temperature will lead to more specific annealing of the primer to its perfectly matched template, which in turn increases the likelihood of amplifying the target sequence only. On the other hand, more mismatches between the template and primer can be tolerated at lower annealing temperatures. In consideration of such phenomenon, adjusting the annealing temperature can alter the specificity of pairing of the template and primer. For example, if there is no product, the temperature may be too high for annealing. If there are several products different in size where only one primer is present, this indicates that the single primer is annealing to more than one region of the template. In this case, the annealing temperature should be increased.

In addition to annealing temperature, several "primer search parameters", such as primer length, GC content, and PCR product length, should be considered for primer annealing specificity. A primer satisfying all such parameters will result in significant enhancement of primer annealing specificity during target DNA amplification, while resolving the problems of backgrounds and non-specific products arising from primers used in the experiments. It is usual that well-designed primers can help avoid non-specific annealing and backgrounds as well as distinguish between cDNAs or genomic templates in RNA-PCR.

Many approaches have been developed to improve primer annealing specificity and therefore accomplish the amplification of the desired product. Examples are touchdown PCR (Don et al., (1991) Touchdown PCR to circumvent spurious priming during gene amplification. *Nucleic Acids Res.,* 19, 4008), hot start PCR (DAquila et al., (1991) Maximizing sensitivity and specificity of PCR by pre-amplification heating. *Nucleic Acids Res.,* 19, 3749), nested PCR (Mullis and Faloona, (1987) Specific synthesis of DNA in vitro via a polymerase-catalyzed chain reaction. *Methods Enzymol* 155, 335-350), and booster PCR (Ruano et al., (1989) Biphasic amplification of very dilute DNA samples via booster PCR. *Nucleic Acids Res.* 17, 540). Other alternative approaches have been also reported that various 'enhancer' compounds can improve the specificity of PCR. The enhancer compounds include chemicals that increase the effective annealing temperature of the reaction, DNA binding proteins, and commercially available reagents. However, there is no 'magic' additive that will ensure the success in every PCR, and it is very tedious to test different additives under different conditions such as annealing temperature. Although these approaches have contributed to the improvement of primer annealing specificity in some cases, they have not accessed fundamentally to a solution for the problems arising from primers used in the PCR amplification, such as non-specific products and high backgrounds.

PCR-based techniques have been widely used not only for amplification of a target DNA sequence, but also for scientific applications or methods in the fields of biological and medical research, such as reverse transcriptase PCR (RT-PCR), differential display PCR (DD-PCR), cloning of known or unknown genes by PCR, rapid amplification of cDNA ends (RACE), arbitrary priming PCR (AP-PCR), multiplex PCR, SNP genome typing, and PCR-based genomic analysis (McPherson and Moller, (2000) PCR. BIOS Scientific Publishers, Springer-Verlag New York Berlin Heidelberg, NY).

As described above, all these methods and techniques involving nucleic acid amplification, notably PCR amplification, could not be completely free from the limitations and problems resulting from the non-specificity of the primers used in each method, such as false positives, poor reproducibility, high backgrounds, although improved approaches to each method have been continuously introduced. Therefore, there remains a need of novel primer and methods for improving annealing specificity, which can give rise to true amplification results.

Meanwhile, DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis. For example, Wallace and coworkers showed that sequence differences as subtle as a single base change are sufficient to enable discrimination of short (e.g., 14-mer) oligomers and demonstrated how this could be applied in molecular analysis of point mutation in the β-globin gene (Wallace, B. R., et al., (1981) The use of synthetic oligonucleotides as hybridization probes. Hybridization of oligonucleotides of mixed sequence to rabbit β-globin DNA. *Nucleic Acids Res.* 9, 879-894; and Conner, B. J., et al. (1983) Detection of sickle cell β-globin allele by hybridization with synthetic oligonucleotides. *Proc. Natl. Acad. Sci. USA* 80, 278-282).

In spite of the power of oligonucleotide hybridization to correctly identify a complementary strand, researchers still face limitations. Hybrids containing oligonucleotides are much less stable than hybrids of long nucleic acids. This is reflected in lower melting temperature. The instability of the hybrids is one of the most important factors to be considered when designing oligonucleotide hybridization. The stability difference between a perfectly matched complement and a complement mismatched at only one base can be quite small, corresponding to as little as 0.5° C. difference in their $T_m$s (duplex melting temperature). The shorter the oligomer of interest (permitting identification of a complementary strand in a more complex mixture), the stronger the effect of a single-base mismatch on overall duplex stability. However, the disadvantage of using such short oligonucleotides is that they hybridize weakly, even to a perfectly complementary sequence, and thus must be used under the conditions of reduced stringency, which results in decreasing hybridization specificity seriously.

There have been many efforts to improve the specificity of oligonucleotide hybridization. A method for chemically modifying bases of DNA for high-sensitivity hybridization (Azhikina et al., (1993) *Proc. Natl. Acad. Sci., USA,* 90:11460-11462) and a method in which the washing after the hybridization is conducted at low temperatures for a long period to enhance the ability of discriminating the mismatch (Drmanac et al., (1990) *DNA and Cell Biology,* 9:527-534) have been proposed. Recently, another method has been introduced for increasing the resolution power of single nucleotide polymorphisms (SNPs) in DNA hybridization by means of artificial mismatches (Guo et al., (1997) *Nature Biotechnology,* 15:331-5). In addition, many U.S. patents including U.S. Pat. Nos. 6,077,668, 6,329,144, 6,140,054, 6,350,580, 6,309,824, 6,342,355 and 6,268,128 disclose the probe for hybridization and its applications. Although the improved approaches to each method have been continuously introduced, all these methods and techniques involving oligonucleotide hybridization could not be completely free from the limitations and problems arising from non-specificity of oligonucleotide hybridization.

There is still a possibility that artificial factors, such as the failures of spotting and immobilization of oligonucleotide on substrate and establishment of optimal hybridization conditions, would affect the negative data of hybridization; the effect of erroneous results is more vulnerable to the results generated from high-throughput screening method. Such artificial factors inherent to spotting and hybridization are main practical drawbacks in oligonucleotide-based DNA microarrays.

Furthermore, the development of DNA sequence determination techniques with enhanced speed, sensitivity, and throughput are of utmost importance for the study of biological systems. Conventional DNA sequencing technique originally developed more than two decades ago (Sanger et al. (1977) *Proc. Natl. Acad. Sci.,* 74:5463-5467) faces limitations in both throughput and cost for future applications.

Therefore, several new techniques have been proposed. Three methods that hold great promise are sequencing by hybridization (Brain and Smith, (1988) *J. Theor. Biol.,* 135:303-307); Drmanac et al., (1989) Genomics, 4:114-128); and Southern, E. M. (1989) Patent WO/10977), parallel signature sequencing based on ligation and cleavage (Brenner et al., (2000) *Proc. Natl. Acad. Sci.,* 97:1665-1670), and pyrosequencing (Ronaghi et al., (1996) *Anal. Biochem.,* 242:84-89; and (1998) *Science* 281:363-365). For all aforementioned techniques, the success of sequencing reactions absolutely depends upon the hybridization specificity of the sequencing primer to a target nucleic acid. In consideration of the hybridization specificity of the sequencing primer, current methods are subject to limitation of the length of template nucleic acids supplied for sequencing reactions. In general, sequencing reactions are conducted using template nucleic acids preferably less than a few hundred base pairs in length such that the specific hybridization of the sequencing primer is achieved to certain extent.

For advanced studies, however, DNA sequencing reactions with enhanced speed, sensitivity, and throughput should not be hindered by the size of template nucleic acids. In light of this, direct sequencing of a target nucleic acid from a population of template nucleic acid is allowed, provided that the sequencing primers are hybridized with the target nucleic acids at high specificity.

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

To eliminate the problems and shortcomings of such conventional oligonucleotides, used as primers or probes, and various methods involving nucleic acid hybridization, the present inventor has developed a dual specificity oligonucleotide that allows a template-dependent reaction to proceed with much higher specificity and found its excellent applications to a wide variety of processes involving oligonucleotide hybridization or annealing.

Accordingly, it is an object of this invention to provide a method for synthesizing a nucleic acid molecule using a dual specificity oligonucleotide by a template-dependent extension reaction.

It is another object of this invention to provide a method for selectively amplifying a target nucleic acid sequence from a DNA or a mixture of nucleic acids.

It is still another object of this invention to provide a method for amplifying two or more target nucleotide sequences simultaneously using two or more pairs of primers in the same reaction.

It is further object of this invention to provide a method for sequencing a nucleic acid molecule from a DNA or a mixture of nucleic acids.

It is still further object of this invention to provide a method for detecting a nucleic acid molecule with genetic diversity by a template-dependent extension reaction.

It is another object of this invention to provide a method for detecting a target nucleotide sequence in a nucleic acid sample by use of dual specificity oligonucleotide-immobilized microarray.

It is still another object of this invention to provide a dual specificity oligonucleotide for synthesizing a nucleic acid molecule by a template-dependent extension reaction.

It is further object of this invention to provide a method for enabling an annealing specificity of an oligonucleotide to be dually determined through a structure of the oligonucleotide.

It is still further object of this invention to provide a method for improving an annealing specificity of an oligonucleotide.

Other objects and advantages of the present invention will become apparent from the detailed description to follow taken in conjugation with the appended claims and drawings.

BRIEF DESCRIPTION OF THE DRAWINGS

FIGS. 1A and 1B schematically represent the principle of the dual specificity (DS) oligonucleotide of this invention in a template-dependent extension reaction. FIG. 1A shows high hybridization specificity of the DS oligonucleotide under high stringency conditions. FIG. 11B shows mismatch tolerance of the DS oligonucleotide.

FIG. 4 shows schematic representations for template-dependent extension reactions in selective determination of a target nucleic acid using dual specificity oligonucleotides on oligonucleotide microarray.

FIG. 6A is an agarose gel photograph showing the results of the 3'-RACE (rapid amplification of cDNA ends) of the DEG 10 gene, demonstrating PCR specificity of the dual specificity oligonucleotide. Lane 1 represents a primer with perfect match sequence, lanes 2-4 represent primers with 3, 2 and 1 base mismatch at its 3'-low $T_m$ specificity portion, respectively, and lanes 5-7 represent primers with 5, 3 and 2 base mismatch at its 5'-high $T_m$ specificity portion, respectively. M is a 100-bp size marker generated by Forever 100-bp Ladder Personalizer.

FIG. 7A represents the sequences of 5' primers for 3'-RACE of the mouse placenta-specific homeobox family genes Psx1 and Psx2. Psx1-5'-40 and Psx2-5'-40 are conventional primers and Psx1-5'-41 and Psx2-5'-41 are primers designed according to the present invention.

DETAILED DESCRIPTION OF THIS INVENTION

Figure 2:
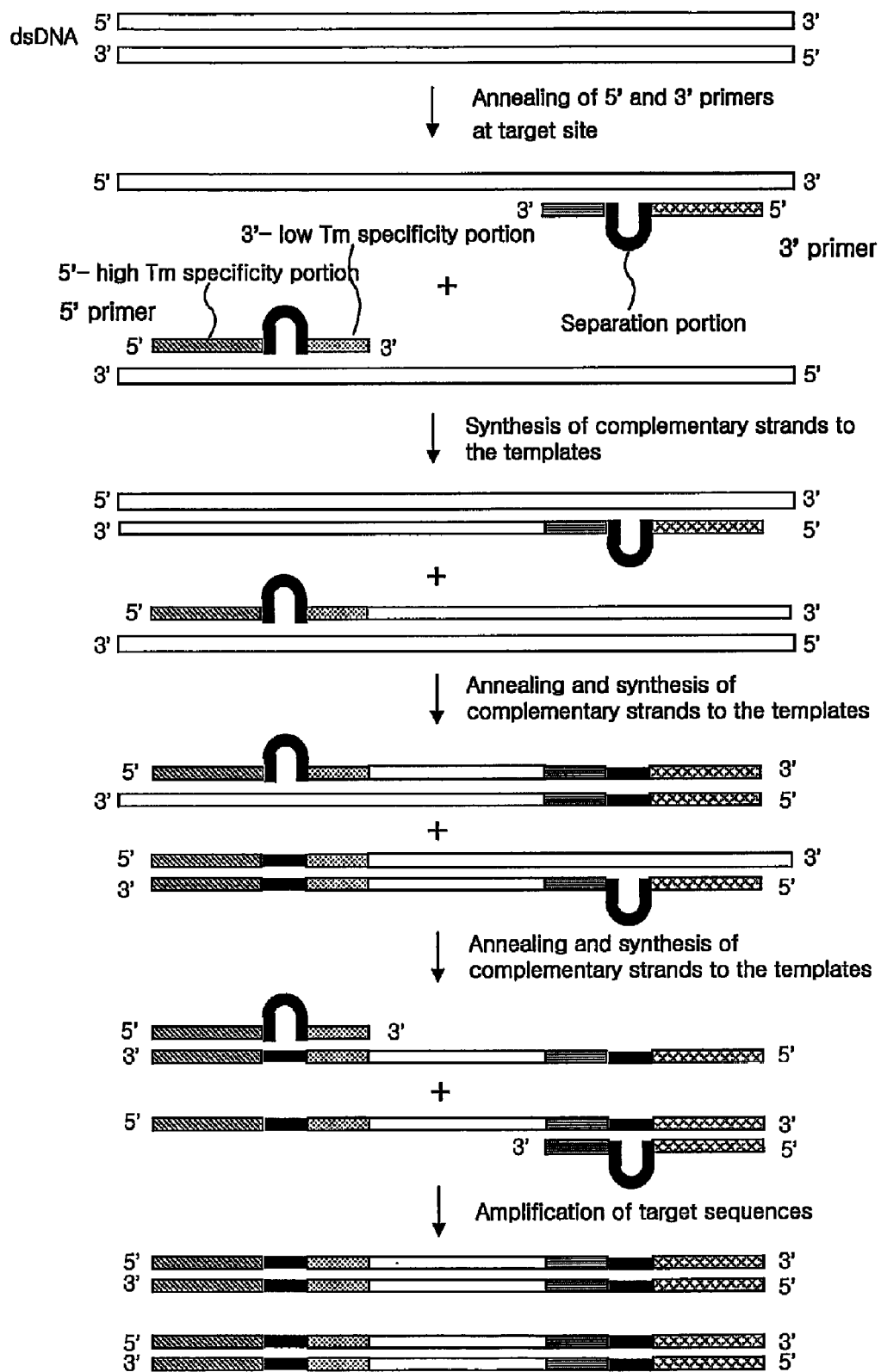
FIG. 2 shows schematic representations for selectively amplifying a target nucleic acid of double-strand DNA using DS oligonucleotide primers of this invention.

The present invention is generally directed to (a) a wide variety of processes using a dual specificity oligonucleotide and (b) a dual specificity oligonucleotide therefor. The dual specificity oligonucleotide of this invention (hereinafter referred to as "DS oligo") allows primer or probe to be annealed to its target sequence with improved specificity, such that the specificity of nucleic acid amplification (in particular, PCR) and hybridization reaction can be significantly improved.

Dual Specificity Oligonucleotide (DS Oligo)

In one aspect of this invention, there is provided a dual specificity oligonucleotide for synthesizing a nucleic acid molecule by a template-dependent extension reaction, which is represented by the following general formula:

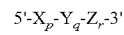

$$5'\text{-}X_p\text{-}Y_q\text{-}Z_r\text{-}3'$$

wherein, $X_p$ represents a 5'-high $T_m$ specificity portion having a hybridizing nucleotide sequence substantially complementary to a site on a template nucleic acid to hybridize therewith, $Y_q$ represents a separation portion comprising at least two universal bases, $Z_r$ represents a 3'-low $T_m$ specificity portion having a hybridizing nucleotide sequence substantially complementary to a site on the template nucleic acid to hybridize therewith, p, q and r represent the number of nucleotides, and X, Y, and Z are deoxyribonucleotide or ribonucleotide; $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the template nucleic acid, enabling the 5'-high $T_m$ specificity portion to separate from the 3'-low $T_m$ specificity portion in terms of annealing specificity to the template nucleic acid, whereby the annealing specificity of the oligonucleotide is determined dually by the 5'-high $T_m$ specificity portion and the 3'-low $T_m$ specificity portion such that an overall annealing specificity of the oligonucleotide is enhanced.

The term "dual specificity" with referring to the DS oligonucleotide (hereinafter referred to as "DS oligo") of this invention used herein is coined to describe its prominent feature that its annealing specificity to a target sequence is dually determined by its separate two portions, i.e., the 5'-high $T_m$ specificity portion and the 3'-low $T_m$ specificity portion. In general, the annealing specificity of primers or probes is governed by their overall consecutive sequence. In contrast, the annealing specificity of the DS oligo is dually determined by its two portions (the 5'-high $T_m$ specificity portion and the 3'-low $T_m$ specificity portion) separated by the separation portion, in which these three portions are located in one oligonucleotide sequence. Such dual specificity permits the DS oligo to serve as a primer and probe exhibiting much higher specificity, rendering the present invention to be novel and unobvious over prior art.

Meanwhile, the present inventor has already developed the ACP (annealing control primer) to improve annealing specificity as disclosed in WO 03/050303, the teachings of which are incorporated herein by reference. The DS oligo of this invention is distinctly different from the ACP in light of the following: (i) the DS oligo has two specificity portions to be hybridized with a target sequence whereas the ACP has one specificity portion; (ii) three portions in the DS oligo are distinctly discriminated in view of $T_m$ whereas portions in the ACP are not; (iii) the DS primer is extended to synthesize a nucleic acid molecule complementary to the template only when annealing occurs by both the 5'-high $T_m$ specificity portion and 3'-low $T_m$ specificity portion, whereas the ACP is extended even when annealing occurs by the 3'-end portion; and (iv) thus the annealing or hybridizing specificity of the DS oligo is determined dually by the two separate portions, i.e., the 5'-high $T_m$ specificity portion and the 3'-low $T_m$ specificity portion, whereas that of the ACP is governed only by the 3'-end portion. Accordingly, it could be appreciated that the annealing or hybridizing specificity of the DS oligo to its target sequence is much higher than that that of the ACP, addressing that the DS oligo is novel and unobvious over the ACP.

The striking feature of the DS oligo is to have three different portions with distinct properties within one oligonucleotide molecule: 5'-high $T_m$ specificity portion, 3'-low $T_m$ specificity portion and separation portion.

The DS oligo is useful in a wide variety of processes and analyses involving a template-dependent extension reaction. The term used herein "a template-dependent extension reaction" means a reaction to extend an oligonucleotide molecule hybridized to a target sequence by incorporating successive nucleotides into its end moiety in which the extended sequence is determined by a complementary template sequence.

A schematic representation for the principles governing the hybridization (annealing) specificity of the DS oligo is illustrated in FIG. 1A. Referring to FIG. 1A, the DS oligo will be described in more detail.

Where only the 5'-high $T_m$ specificity portion of the DS oligo is annealed to a template, it cannot serve as a priming site for a template-dependent extension, resulting in no occurrence of extension.

While the 5'-high $T_m$ specificity portion of the DS oligo is annealed to a non-target sequence, the 3'-low $T_m$ specificity portion having a shorter sequence is unlikely to anneal to the non-target sequence. The reasons for that are that the 5'-high $T_m$ specificity portion and the 3'-low $T_m$ specificity portion are separated by the separation portion in terms of annealing events. In other words, the 3'-low $T_m$ specificity portion is involved in annealing events in a relatively independent manner from the 5'-high $T_m$ specificity portion and the annealing of the 3'-low $T_m$ specificity portion is less affected by the annealing of the 5'-high $T_m$ specificity portion. In this connection, the likelihood of annealing of the 3'-low $T_m$ specificity portion to a non-target sequence becomes much lower.

Where only the 3'-low $T_m$ specificity portion has a sequence complementary to a non-target site, annealing either does not occur under certain high stringent conditions, e.g., stringent conditions for annealing of the 5'-high $T_m$ specificity portion. According to a preferred embodiment, it is advantageous to perform template-dependent extension reactions using the DS oligo under stringent conditions with annealing temperature much higher than $T_m$ of the 3'-low $T_m$ specificity portion.

Where both 5'-high $T_m$ specificity portion and 3'-low $T_m$ specificity portion have a sequence substantially complementary to a template, the DS oligo can be annealed to the template and hence the successful extension occurs.

Without wising to be bound by theory, it is believed that the separation portion makes the 3'-low $T_m$ specificity portion more sensitive to annealing conditions (e.g., temperature and sequence complementarity). In this regard, the incidence of the non-specific hybridization between the 3'-low $T_m$ specificity portion and non-target sequences becomes much lower under certain annealing (or stringent) conditions. Where the 3'-low $T_m$ specificity portion as well as the 5'-high $T_m$ specificity portion is annealed to its target sequence, the 3'-end of the 3'-low $T_m$ specificity portion is more likely to generate a site extendible by DNA polymerases.

The term "oligonucleotide" as used herein refers to a linear oligomer of natural or modified monomers or linkages, including deoxyribonucleotides, ribonucleotides and the like, capable of specifically hybridizing with a target nucleotide sequence, whether occurring naturally or produced synthetically. The oligonucleotide is preferably single stranded for maximum efficiency in hybridization. Preferably, the oligonucleotide is an oligodeoxyribonucleotide. The oligonucleotide of this invention can be comprised of naturally occurring dNMP (i.e., dAMP, dGM, dCMP and dTMP), nucleotide analogs, or nucleotide derivatives. The oligonucleotide can also include ribonucleotides. For example, the oligonucleotide of this invention may include nucleotides with backbone modifications such as peptide nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide. The primer of this invention can be comprised of naturally occurring dNMP (i.e., dAMW, dGM, dCMP and dTMP), modified nucleotide, or non-natural nucleotide. The primer can also include ribonucleotides. The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof. The term used "hybridizing" used herein refers to the formation of a double-stranded nucleic acid from complementary single stranded nucleic acids. There is no intended distinction between the terms "annealing" and "hybridizing", and these terms will be used interchangeably.

The term used herein "probe" refers to a single-stranded nucleic acid molecule comprising a portion or portions that are substantially complementary to a target nucleotide sequence.

The term "portion" used herein in conjunction with the DS oligo of this invention refers to a nucleotide sequence separated by the separation portion. The term "5'-high $T_m$ specificity portion" or "3'-low $T_m$ specificity portion" refers to a nucleotide sequence at the 5'-end or 3'-end of the DS oligo of this invention, respectively, which is separated by the separation portion. The term "5'-high $T_m$ specificity portion" in conjunction with the DS oligo is intended to refer to a portion with the highest $T_m$ among three portions and having a hybridizing nucleotide sequence substantially complementary to a site on the template nucleic acid. The term "3'-low $T_m$ specificity portion" in reference to the DS oligo means a portion with a lower $T_m$ than the 5'-high $T_m$ specificity portion but higher $T_m$ than the separation portion and having a hybridizing nucleotide sequence substantially complementary to a site on the template nucleic acid.

The term "$T_m$" used herein refers to the melting temperature at which half the molecules of a nucleic acid duplex are single stranded. The terms "high $T_m$" and "low $T_m$" in conjunction with portions in the DS oligo are intended to describe a relative $T_m$ value yet not an absolute $T_m$ value. That is, it is only required that the $T_m$ of the 5'-high $T_m$ specificity portion is high relative to that of the 3'-low $T_m$ specificity portion.

The 5'-high $T_m$ specificity portion and 3'-low $T_m$ specificity portion are designed to have a hybridizing nucleotide sequence substantially complementary to a site on a template nucleic acid to hybridize therewith. The term "substantially complementary" in reference to the DS oligo is used herein to mean that the oligonucleotide molecule is sufficiently complementary to hybridize selectively to a template nucleic acid sequence under the designated annealing conditions or stringent conditions, such that the annealed oligonucleotide can be extended by a polymerase to form a complementary copy of the template. Therefore, this term has a different meaning from "perfectly complementary" or related terms thereof. It will be appreciated that the 5'-high $T_m$ specificity portion and 3'-low $T_m$ specificity portion of the DS oligo can have one or more mismatches to a template to an extent that the DS oligo can serve as primer or probe. Most preferably, the 5'-high $T_m$ specificity portion and/or 3'-low $T_m$ specificity portion of the DS oligo have a nucleotide sequence perfectly complementary to a site on a template, i.e., no mismatches.

For successful performance of the DS oligo, it is essential that the $T_m$ of the 5'-high $T_m$ specificity portion is higher than that of the 3'-low $T_m$ specificity portion. It is preferred that the $T_m$ of the 5'-high $T_m$ specificity portion ranges from 40° C. to 80° C., more preferably, 40° C. to 75° C., still more preferably, 50° C. to 68° C., and most preferably, 50° C. to 65° C. It is preferred that $T_m$ of the 3'-low $T_m$ specificity portion ranges from 10° C. to 40° C., more preferably, 15° C. to 40° C., and most preferably, 20° C. to 35° C. Preferably, the $T_m$ of the 5'-high $T_m$ specificity portion is higher at least 5° C., more preferably at least 110° C., still more preferably at least 15° C., and most preferably at least 20° C. than that of the 3'-low $T_m$ specificity portion. Advantageously, the $T_m$ of the 5'-high $T_m$ specificity portion is higher 5-70° C., preferably, 10-70° C., more preferably, 10-60° C., still more preferably, 10-50° C., still yet more preferably, 10-40° C. and most preferably, 20-40° C. than that of the 3'-low $T_m$ specificity portion.

According to a preferred embodiment, the 5'-high $T_m$ specificity portion is longer than the 3'-low $T_m$ specificity portion. The length of 5'-high $T_m$ specificity portion is preferably 15 to 40 nucleotide residues, more preferably, 15 to 30 nucleotide residues, and most preferably, 20 to 25 nucleotide residues. The length of 3'-low $T_m$ specificity portion is preferably 3 to 15 nucleotide residues, more preferably, 5 to 15 nucleotide residues, and most preferably, 6 to 12 nucleotide residues.

The separation portion comprising at least two universal bases is partly responsible for advantages and features of the DS oligo. The term "universal base" used herein refers to one capable of forming base pairs with each of the natural DNA/RNA bases with little discrimination between them.

It has been widely known that nucleotides at some ambiguous positions of degenerate primers have been replaced by universal base such as deoxyinosine (Ohtsuka, E. et al., (1985) *J. Biol. Chem.* 260, 2605-2608; and Sakanari, S. A. et al., (1989) *Proc. Natl. Acad. Sci.* 86, 4863-4867), 1-(2'-deoxy-beta-D-ribofuranosyl)-3-nitropyrrole (Nichols, R. et al., (1994) *Nature* 369, 492-493) and 5-nitroindole (Loakes, D. et al., (1994) *Nucleic Acids Res.* 22, 4039-4043) for solving the design problems associated with the degenerate primers, because such universal bases are capable of non-specific base pairing with all four conventional bases. However, there has not been any report that these universal bases allow forming a portion in an oligonucleotide molecule to generate a bubble structure during annealing (hybridization) or amplification and then separate two opposite adjacent sequences, resulting in the elevation of the annealing specificity of primer or probe to a target sequence by dual specificity through two separate specificity (annealing) portions.

According to a preferred embodiment, the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole, and combinations thereof. More preferably, the universal base or non-discriminatory base analog is deoxyinosine, 1-(2'-deoxy-beta-D-ribofuranosyl)-3-nitropyrrole or 5-nitroindole, most preferably, deoxyinosine.

Such universal bases may be contained in the separation portion in a contiguous manner or interrupted manner with other nucleotides such as dNMPs. It is preferable that the separation portion comprises contiguous nucleotides having universal bases, preferably, deoxyinosine.

It is critical that the separation portion in the DS oligo has the lowest $T_m$ in the three portions, in order that the separation portion forms a non base-pairing bubble structure under conditions that the 5'-high $T_m$ specificity portion and the 3'-low $T_m$ specificity portion are annealed to the template nucleic acid, enabling the 5'-high $T_m$ specificity portion to separate from the 3'-low $T_m$ specificity portion in terms of annealing specificity to the template nucleic acid, whereby the annealing specificity of the oligonucleotide is determined dually by the 5'-high $T_m$ specificity portion and the 3'-low $T_m$ specificity portion such that the overall annealing specificity of the oligonucleotide is considerably enhanced. Preferably, the $T_m$ of the separation portion ranges from 3° C. to 15° C., more preferably, 4° C. to 15° C., and most preferably 5° C. to 10° C.

According to a preferred embodiment, the separation portion between the 5'-high $T_m$ specificity portion and the 3'-low $T_m$ specificity portion contains at least 3 universal bases, more preferably at least 4 universal bases, and most preferably at least 5 universal bases. According to a preferred embodiment, the separation portion contains 2-10 universal bases, more preferably 3-10 universal bases, still more preferably, 4-8 universal bases, and most preferably, 5-7 universal bases.

Where a primer or probe having a longer sequence is required, the advantages of the DS oligo are most highlighted. For example, according to a conventional technique, a primer having a nucleotide sequence longer than 35 bp as a hybridizing sequence is very liable to generate non-specific amplicons. By contrast, the DS oligo can generate specific amplicons even with long sequences, since it carries two hybridizing sequences (i.e., the 5'-high $T_m$ specificity portion and the 3'-low $T_m$ specificity portion) separated from each other in terms of molecular interaction with templates (i.e., annealing). For example, the DS oligo may contain 35-45 bp of a hybridizing sequence complementary to a target sequence. In this regard, it could be appreciated that the present invention permits primers to be designed with much longer sequences considered to be non-practicable in conventional primer design strategies.

According to a preferred embodiment, the 5'-high $T_m$ specificity portion is 15 to 25 nucleotides in length, the separation portion is 3 to 15 nucleotides in length, and the 3'-low $T_m$ specificity portion is 3 to 15 nucleotides in length.

More preferably, the 5'-high $T_m$ specificity portion is 15 to 25 nucleotides in length; the separation portion is 3 to 10 nucleotides in length; and the 3'-low $T_m$ specificity portion is 5 to 15 nucleotides in length. Most preferably, the 5'-high $T_m$ specificity portion is 15 to 25 nucleotides in length; the separation portion is 5 to 7 nucleotides in length; and the 3'-low $T_m$ specificity portion is 6 to 10 nucleotides in length. According to the exemplary and illustrative DS oligo described in Examples, the 5'-high $T_m$ specificity portion is about 20 nucleotides in length; the separation portion is about 5 nucleotides in length; and the 3'-low $T_m$ specificity portion is about 8-10 nucleotides in length.

In the most preferred embodiment, the DS oligo is represented by the following general formula: 5'-$X_p$-(dI)$_q$-$Z_r$-3' (definition and characteristics of $X_p$ and $Z_r$ are the same as described previously, $d^1$ represents deoxyinosine, (dI)$_q$ represents a separation portion comprising contiguous nucleotides having universal bases and q is an integer between 5-7).

Interestingly, the present DS oligo also has mismatch tolerance under the stringent conditions sufficient to tolerate mismatching to its target sequence.

A schematic representation for the principles governing mismatch tolerance of the DS oligo is illustrated in FIG. 1B. One or more, preferably one to three base mismatches in the 5'-high $T_m$ specificity portion can be tolerated under the condition that both 5'-high $T_m$ specificity portion and 3'-low $T_m$ specificity portion are annealed to the template. One or more, preferably one to two base mismatches in the 3'-low $T_m$ specificity portion can be tolerated under the condition that both 5'-high $T_m$ specificity portion and 3'-low $T_m$ specificity portion are annealed to the template. Further, one or more, preferably one to five base mismatches in both the 5'-high $T_m$ specificity portion and 3'-low $T_m$ specificity portion can be tolerated under the condition that both 5'-high $T_m$ specificity portion and 3'-low $T_m$ specificity portion are annealed to the template.

For imposing mismatch tolerance on the DS oligo, the annealing condition, notably, the annealing temperature is important. The annealing is performed under conditions that annealing solely by the 3'-low $T_m$ specificity portion does not occur, yet annealing by all the portions occurs when the 5'-high $T_m$ specificity portion and/or the 3'-low $T_m$ specificity portion has one or more, yet limited, mismatched bases to its target site. The DS oligos having mismatch tolerance is required to amplify or detect a nucleotide sequence with genetic diversity. The DS oligos with mismatch tolerance can be annealed to target sequences showing genetic diversity and result in successful amplification and detection of nucleotide sequences of interest. In other words, the DS oligo originally developed to dramatically enhance specificity of annealing and hybridization can be also used in processes to require mismatch tolerance where annealing or stringent conditions are suitably adjusted.

In another aspect of this invention, there is provided a method for enabling an annealing specificity of an oligonucleotide to be dually determined through a structure of the oligonucleotide, which comprises the steps of: (a) selecting a target nucleic acid sequence; (b) designing a sequence of an oligonucleotide having (i) a hybridizing sequence substantially complementary to the target nucleic acid and (ii) a separation portion comprising at least two universal bases, such that the separation portion intervenes in the hybridizing sequence to form three portions in the oligonucleotide; and (c) determining the position of the separation portion in the oligonucleotide to allow a portion at the 5'-direction of the separation portion to have a higher $T_m$ than a portion at the 3'-direction of the separation portion and to allow the separation portion to have the lowest $T_m$ in the three portions, thereby providing an oligonucleotide having three distinct portions with different $T_m$ values from one another in which (i) a 5'-high $T_m$ specificity portion of the oligonucleotide has a hybridizing nucleotide sequence substantially complementary to the target nucleic acid, (ii) a 3'-low $T_m$ specificity portion of the oligonucleotide has a hybridizing nucleotide sequence substantially complementary to the target nucleic acid; and (iii) the separation portion of the oligonucleotide between the 5'-high $T_m$ specificity portion and 3'-low $T_m$ specificity portion comprises at least two universal bases; and the $T_m$ of the 5'-high $T_m$ specificity portion is higher than that of the 3'-low $T_m$ specificity portion and the separation portion has the lowest $T_m$ in the three portions, whereby the annealing specificity of the oligonucleotide to the target nucleic acid is determined dually by both the 5'-high $T_m$ specificity portion and the 3'-low $T_m$ specificity portion.

The present method is directed to provide a novel approach to dramatically increase the annealing specificity of an oligonucleotide to be hybridized with its target sequence. The present method is also expressed as a method for improving an annealing specificity of an oligonucleotide. Moreover, the present invention is expressed as a method using a separation portion comprising at least two universal bases for improving the annealing specificity of an oligonucleotide hybridized to a target sequence.

The present method is performed to prepare the DS oligo discussed hereinabove. Therefore, in the interest of avoiding unnecessary redundancy, the common descriptions between them are not being repeated but they are incorporated into this description of the method as if they were repeated.

Most of the conventional methods for designing primers or probes merely use a sequence as hybridizable to their target sequences as available. Moreover, to increase the annealing specificity of oligonucleotides, it has been conventionally attempted to adjust amplification or hybridization conditions such as temperature and ion concentration.

By contrast, the present method provides a novel strategy for increasing annealing specificity by introducing novel characteristics into oligonucleotide sequences per se. The term "through a structure of the oligonucleotide" used herein with reference to enabling the annealing specificity of oligonucleotides to be dually determined means that the structure of oligonucleotides contributes heavily to the increase in the annealing specificity of oligonucleotides by imposing on oligonucleotides a novel feature to be dually determined in terms of annealing specificity.

It is critical in the present method to design a sequence of an oligonucleotide having (i) a hybridizing sequence substantially complementary to the target nucleic acid and (ii) a separation portion comprising at least two universal bases. In this step, the structural outline of the oligonucleotide is presented to show a 5'-end portion/separation portion/3'-end portion in the oligonucleotide. Both the 5'-end and 3'-end portions carry a hybridizing sequence substantially complementary to the target nucleic acid and are intervened by the separation portion.

The most critical step in the present invention is to determine the position of the separation portion in the oligonucleotide to allow a portion at the 5'-direction of the separation portion to have a higher $T_m$ than a portion at the 3'-direction of the separation portion and to allow the separation portion to have the lowest $T_m$ in the three portions, thereby providing an oligonucleotide having three distinct portions with different $T_m$ values from one another.

The novel structural characteristics introduced into oligonucleotides by the present method are: (i) three distinct portions (5'-high $T_m$ specificity portion, separation portion and 3'-low $T_m$ specificity portion) in oligonucleotide sequences; (ii) different $T_m$ values of the three portions from one another; (iii) separation portion between the 5'-high $T_m$ specificity portion and 3'-low $T_m$ specificity portion comprising at least two universal bases; (iv) two portions involved in molecular interaction with targets in annealing step, which is separated in terms of annealing event by the separation portion; (v) $T_m$ values following the order of the 5'-high $T_m$ specificity portion, 3'-low $T_m$ specificity portion and separation portion. Such structural features ensure the annealing specificity of oligonucleotides finally provided by the present invention to be determined dually by both the 5'-high $T_m$ specificity portion and the 3'-low $T_m$ specificity portion, permitting the dramatic increase in the annealing specificity of oligonucleotides to their target sequence.

The oligonucleotides designed and prepared according to the present method exhibit much higher annealing specificity than those not having such three portions.

The features and advantages of the DS oligo will be described as follows:

(a) the separation portion of the DS oligo comprises at least two universal bases which generates the lowest $T_m$ region in the DS oligo, so that it forms a non base-pairing bubble structure under conditions that the 5'-high $T_m$ specificity portion and the 3'-low $T_m$ specificity portion are annealed to the template nucleic acid. Such non base-pairing bubble structure enables the 5'-high $T_m$ specificity portion to separate from the 3'-low $T_m$ specificity portion in terms of annealing specificity to the template nucleic acid;

(b) the $T_m$ of the 5'-high $T_m$ specificity portion is higher than that of the 3'-low $T_m$ specificity portion, and the separation portion shows the lowest $T_m$, which makes it possible to establish stringent conditions under that annealing solely by the 3'-low $T_m$ specificity portion does not occur;

(c) thus, the overall annealing specificity of the DS oligo is determined dually by both 5'-high $T_m$ specificity portion and 3'-low $T_m$ specificity portion; and (d) consequently, the overall annealing specificity of the DS oligo is dramatically improved.

It may be appreciated that the DS oligo of the present invention is very useful in a variety of (i) primer-based nucleic acid amplification methods such as the methods of Miller, H. I. (WO 89/06700) and Davey, C. et al. (EP 329,822), Ligase Chain Reaction (LCR, Wu, D. Y. et al., *Genomics* 4:560 (1989)), Polymerease Ligase Chain Reaction (Barany, PCR Methods and Applic., 1:5-16 (1991)), Gap-LCR (WO 90/01069), Repair Chain Reaction (EP 439,182), 3SR (Kwoh et al., PNAS, USA, 86:1173 (1989)) and NASBA (U.S. Pat. No. 5,130,238), (ii) primer extension-based technologies such as cycle sequencing (Kretz et al., (1994) *Cycle sequencing. PCR Methods Appl.* 3:S107-S 112) and pyrosequencing (Ronaghi et al., (1996) *Anal. Biochem.*, 242:84-89; and (1998) *Science* 281:363-365), and (iii) hybridization-based technologies such as detection of a target nucleotide sequence using oligonucleotide microarray. The DS oligo of the subject invention can be applied to a variety of nucleic acid amplification, sequencing and hybridization-based technologies. Representative examples to prove the effect of the DS oligo are as follows:

I. Application to Synthesizing a Nucleic Acid Molecule

In another aspect of this invention, there is provided a method for synthesizing a nucleic acid molecule using a dual specificity oligonucleotide by a template-dependent extension reaction, which comprises the steps of:

(a) annealing the dual specificity oligonucleotide to a template nucleic acid molecule, wherein the dual specificity oligonucleotide has three portions in which a 5'-high $T_m$ specificity portion has a hybridizing nucleotide sequence substantially complementary to a site on the template nucleic acid to hybridize therewith, a separation portion comprises at least two universal bases and a 3'-low $T_m$ specificity portion has a hybridizing nucleotide sequence substantially complementary to a site on the template nucleic acid to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the template nucleic acid, wherein the annealing is performed under conditions that annealing solely by the 3'-low $T_m$ specificity portion does not occur; and (b) extending the dual specificity oligonucleotide to synthesize a nucleic acid molecule complementary to the template nucleic acid.

Since the synthesis method of this invention employs the DS oligo of this invention, the common descriptions between them are omitted in order to avoid the complexity of this specification leading to undue multiplicity.

This application using the DS oligo of the subject invention can provide an improved method for selectively synthesizing a nucleic acid sequence complementary to a target sequence by a template-dependent extension reaction involving annealing and extending steps. In particular, the synthesis of a nucleic acid sequence complementary to a target sequence can be achieved by repeating the process of the template-dependent extension reaction in which the annealing and extension steps are followed by denaturation step.

The method of the present invention can be used to synthesize a nucleic acid molecule complementary to any template nucleic acid molecule. Such molecule may be either DNA or RNA. The molecule may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA is used. The oligonucleotide dT primer is comprised of dTMPs, one or more of which may be replaced with other dNMPs so long as the dT primer can serve as primer. Reverse transcription can be done with reverse transcriptase that has RNase H activity. If one uses an enzyme having RNase H activity, it may be possible to omit a separate RNase H digestion step by carefully choosing the reaction conditions.

The present methods do not require that the template nucleic acid molecules have any particular sequence or length. In particular, the molecules include any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be chemically synthesized. Thus, the nucleic acid sequence may or may not be found in nature.

The DS oligo used for the present invention is hybridized or annealed to a site on the template such that double-stranded structure is formed. Conditions of nucleic acid annealing suitable for forming such double stranded structures are described by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985). The sequences of the 5'-high $T_m$ specificity portion and the 3'-low $T_m$ specificity portion of the DS oligo need not to exhibit precise complementarity, yet need only be substantially complementary in sequence to be able to form a stable double-stranded structure. Thus, departures from complete complementarity are permissible, so long as such departures are not sufficient to completely preclude hybridization to form a double-stranded structure. Annealing of the DS oligo to a site on the template nucleic acid is a prerequisite for its template-dependent polymerization with polymerases. Factors (see Joseph Sambrook, et al., *Molecular Cloning, A Laboratory Manual*, Cold Spring Harbor Laboratory Press, Cold Spring Harbor, N.Y. (2001); and Haymes, B. D., et. al., *Nucleic Acid Hybridization, A Practical Approach*, IRL Press, Washington, D.C. (1985)) which affect the base pairing of the DS oligo to its complementary nucleic acids subsequently affect priming efficiency. The nucleotide composition of the DS oligo can affect the temperature at which annealing is optimal and therefore can affect its priming efficiency.

The 5'-high $T_m$ specificity portion and 3'-low $T_m$ specificity portion of DS oligo during the annealing step play a role as a hybridizing portion or a specificity determining site (i.e., dual specificity determining site), while the separation portion does not serve as a hybridizing site and does not interact with the template for base pairing.

A variety of DNA polymerases can be used in the extension step of the present methods, which includes "Klenow" fragment of *E. coli* DNA polymerase I, a thermostable DNA polymerase, and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis*, and *Pyrococcus furiosus* (Pfu). When a polymerization reaction is being conducted, it is preferable to provide the components required for such reaction in excess in the reaction vessel. Excess in reference to components of the extension reaction refers to an amount of each component such that the ability to achieve the desired extension is not substantially limited by the concentration of that component. It is desirable to provide to the reaction mixture an amount of required cofactors such as $Mg^{2+}$, dATP, dCTP, dGTP, and dTTP in sufficient quantity to support the degree of the extension desired.

Annealing or hybridization in the present method is performed under stringent conditions that allow for specific binding between the DS oligo and the template nucleic acid. Such stringent conditions for annealing will be sequence-dependent and varied depending on environmental parameters. In the present method, the annealing step is generally performed under high stringent conditions. However, if the present method is applied to processes requiring mismatch tolerance, it is preferable that the annealing step is carried out under stringent conditions that the 5'-high $T_m$ specificity portion and the 3'-low $T_m$ specificity portion are annealed to the template despite the presence of one or more, yet limited, base pair mismatches. Such mismatch tolerance is very useful in the amplification or detection of a gene with genetic diversity. Stringent conditions may be readily determined from the standard known in the art.

It is advantageous to perform the annealing step at an annealing temperature higher than the $T_m$ of the 3'-low $T_m$ specificity portion, ensuring that annealing by only the 3'-low $T_m$ specificity portion does not occur. Preferably, the annealing temperature is higher at least 5° C., more preferably at least 10° C., still more preferably at least 15° C., and most preferably at least 20° C. than the $T_m$ of the 3'-low $T_m$ specificity portion.

In a preferred embodiment, the annealing temperature ranges from about 40° C. to 75° C., more preferably, 45° C. to 72° C., still more preferably, 50° C. to 68° C., and most preferably, 55° C. to 65° C. Annealing temperatures suitable in the present method may be determined by considering independently the $T_m$ values of the 5'-high $T_m$ specificity portion and the 3'-low $T_m$ specificity portion. In other words, annealing temperatures in the present method are not be determined by the total length and nucleotide compositions of both the 5'-high $T_m$ specificity portion and the 3'-low $T_m$ specificity portion but by the individual length and nucleotide composition of the 5'-high $T_m$ specificity portion and/or the 3'-low $T_m$ specificity portion. Usually, the annealing temperature determined by considering only the $T_m$ of the 5'-high $T_m$ specificity portion may be much higher than the $T_m$ of the 3'-low $T_m$ specificity portion and become an optimal one.

If mismatch tolerance is required in the annealing step, it is preferred that the annealing temperature is adjusted to become lower than those indicated above.

The present method may be combined with many other processes known in the art to achieve a specific aim. For example, the isolation (or purification) of synthesized product may follow the extension reaction. This can be accomplished by gel electrophoresis, column chromatography, affinity chromatography, or hybridization. In addition, the synthesized product of this invention may be inserted into suitable vehicle for cloning. Furthermore, the synthesized product of this invention may be expressed in a suitable host-harboring expression vector.

II. Application to Amplifying Target Nucleic Acid Sequence

In still another aspect of this invention, there is provided a method for selectively amplifying a target nucleic acid sequence from a DNA or a mixture of nucleic acids, which comprises amplifying the target nucleic acid sequence by performing at least two cycles of primer annealing, primer extending, and denaturing, using a pair of dual specificity oligonucleotides as a primer; wherein the dual specificity oligonucleotide has three portions in which a 5'-high $T_m$ specificity portion has a hybridizing nucleotide sequence substantially complementary to a site on the target nucleic acid to hybridize therewith, a separation portion comprises at least two universal bases and a 3'-low $T_m$ specificity portion has a hybridizing nucleotide sequence substantially complementary to a site on the target nucleic acid to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the target nucleic acid; wherein annealing in the amplification reaction is performed under conditions that annealing solely by the 3'-low $T_m$ specificity portion does not occur.

Since the amplifying method of this invention employs the DS oligo of this invention, the common descriptions between them are omitted in order to avoid the complexity of this specification leading to undue multiplicity. In addition, since this method involves annealing and extension processes, the descriptions as to the two processes are omitted in order to avoid the complexity of this specification leading to undue multiplicity. For instance, the composition and structure of the DS oligo used and the conditions for annealing and extension are common between this process and the method for synthesizing nucleic acid molecule previously discussed.

This application using the DS oligo of the subject invention can provide an improved method for selectively amplifying a target nucleic acid sequence from a nucleic acid or a mixture of nucleic acids (DNA or mRNA) by performing nucleic acid amplifications, preferably, PCR (polymerase chain reaction).

A schematic representation for selectively amplifying a target nucleic acid of double-stranded DNA using the DS oligo as described above is illustrated in FIG. 2. As shown in FIG. 2, one pair of the DS oligos is annealed to a denatured ds DNA template. The 5'-high $T_m$ specificity portion and 3'-low $T_m$ specificity portion during annealing play a role as a hybridizing portion or a specificity determining site (i.e., dual specificity determining site), while the separation portion does not serve as a hybridizing site and not interacted with the template for base pairing. At this time, the separation portion forms a bubble structure in the DS oligo, in order that two end portions, i.e., the 5'-high $T_m$ specificity portion and 3'-low $T_m$ specificity portion can be spatially separated to dually determine the overall specificity of the DS oligo. Details of subsequent reactions are similar to that of conventional primer-based nucleic acid amplifications known in the art described hereinabove.

The present method for amplifying a nucleic acid sequence may be carried out in accordance with various primer-based nucleic acid amplifications known in the art. Preferably, the methods are carried out according to PCR process disclosed in U.S. Pat. Nos. 4,683,195, 4,683,202, and 4,800,159, more preferably, hot start PCR method.

Figure 3:
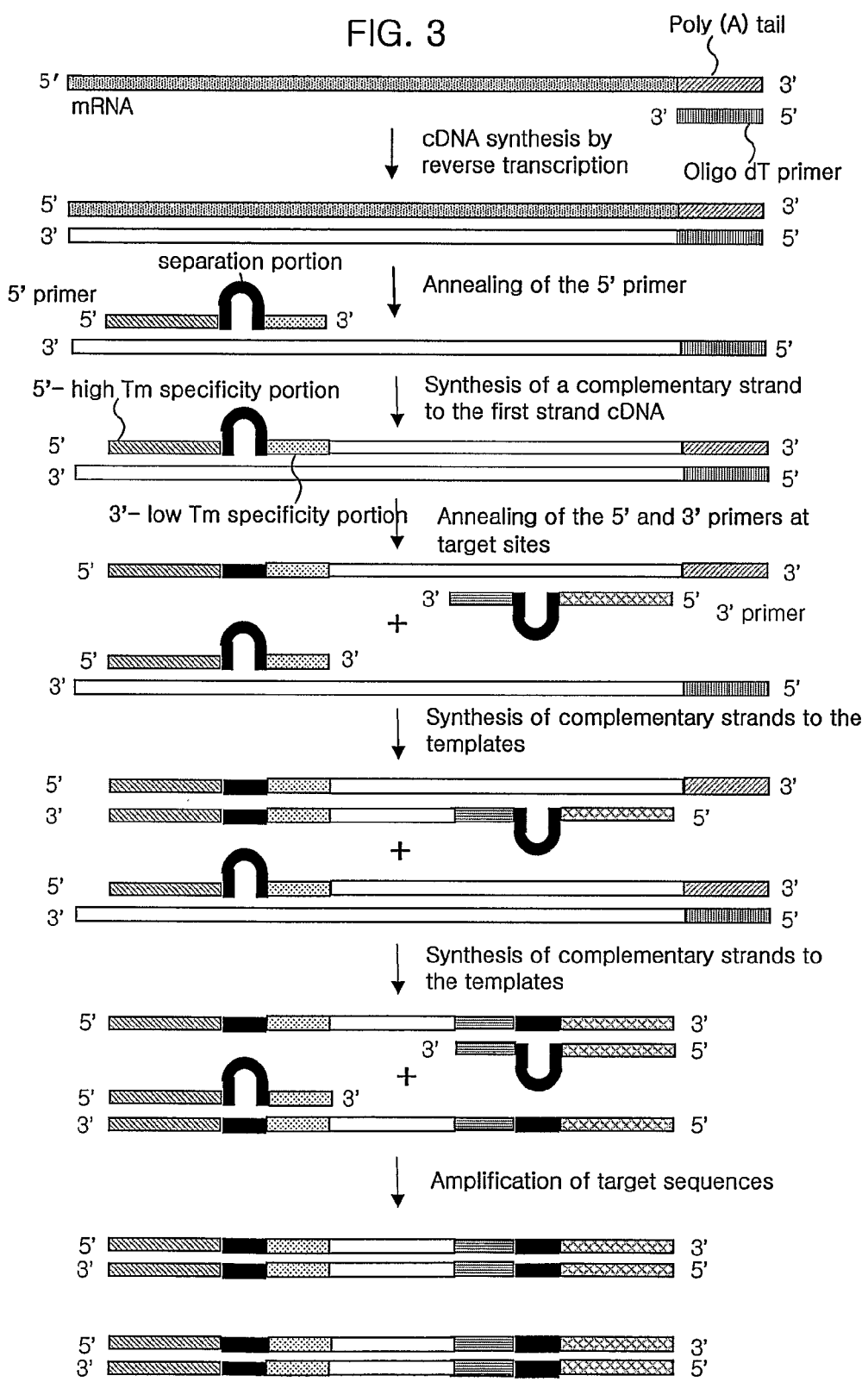
FIG. 3 shows schematic representations for selectively amplifying a target nucleic acid of mRNA using DS oligonucleotide primers of this invention.

FIG. 3 illustrates a schematic representation for selectively amplifying a target nucleic acid of mRNA using the DS oligo. In the first step, mRNA obtained from various biological samples is reverse transcribed using oligo dT primer hybridizable to poly A tail of mRNA and reverse transcriptase. Details of reverse transcription are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). The description of subsequent reactions is similar to that of conventional primer-based nucleic acid amplifications known in the art discussed previously.

III. Application to Multiplex DNA Amplification

In further aspect of this invention, there is provided a method for amplifying two or more target nucleotide sequences simultaneously using two or more pairs of primers in the same reaction, which comprises amplifying the target nucleotide sequences by performing at least two cycles of primer annealing, primer extending and denaturing, using two or more pairs of dual specificity oligonucleotides as a primer, characterized in that the dual specificity oligonucleotides have three portions in which a 5'-high $T_m$ specificity portion has a hybridizing nucleotide sequence substantially complementary to a site on the target nucleotide sequence to hybridize therewith, a separation portion comprises at least two universal bases and a 3'-low $T_m$ specificity portion has a hybridizing nucleotide sequence substantially complementary to a site on the target nucleotide sequence to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the target nucleotide sequence; wherein annealing in the amplification reaction is performed under conditions that annealing solely by the 3'-low $T_m$ specificity portion does not occur.

This application using the DS oligo of the subject invention can also provide an improved method for amplifying more than one target sequence using more than one pair of primers in the same reaction. In general, it is extremely difficult to set up multiplex PCR conditions to amplify more than 10 target sequences in parallel, because an optimal PCR reaction is required to amplify even one specific locus without any unspecific by-products. Since annealing needs to take place at a sufficiently high temperature to allow the perfect DNA-DNA matches to occur in the reaction, the DS oligo of the subject invention is ideal in the optimization of multiplex DNA amplification due to its function of improving the specificity of amplification. "Multiplex PCR" as used herein refers to the simultaneous amplification of multiplex DNA targets in a single polymerase chain reaction (PCR) mixture.

In a specific embodiment of this invention, this Multiplexing process comprises performing an amplification reaction comprising at least two cycles of primer annealing, primer extending and denaturing, using the primer pairs of the DS oligo, characterized in that the primers are a dual specificity oligonucleotide having three portions in which a 5'-high $T_m$ specificity portion has a hybridizing nucleotide sequence substantially complementary to a site on the target nucleotide sequence to hybridize therewith, a separation portion comprises at least two universal bases and a 3'-low $T_m$ specificity portion has a hybridizing nucleotide sequence substantially complementary to a site on the target nucleotide sequence to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the target nucleotide sequence; wherein annealing in the amplification reaction is performed under conditions that annealing solely by the 3'-low $T_m$ specificity portion does not occur.

Since this application using the DS oligo of this invention is carried out in accordance with the present method for amplification of nucleic acid sequence previously discussed, except for using more than one target nucleotide sequence and primer pairs, the common descriptions between them are omitted in order to avoid the complexity of this specification leading to undue multiplicity. For instance, the composition and structure of the DS oligo used and the conditions for amplification, are common between this process and the present methods for amplification of nucleic acid sequence previously discussed.

According to a preferred embodiment, the annealing temperature ranges from about 40° C. to 70° C., more preferably, 45° C. to 68° C., still more preferably, 50° C. to 65° C., and most preferably, 55° C. to 65° C.

In a preferred embodiment, the amplified products from each of target nucleotide sequences are different in size for subsequent analysis. According to a preferred embodiment, the amplification products of multiplex target nucleotide sequences may be analyzed through size separation. The size separation comparison is performed using a variety of method known in the art, such as electrophoresis through a polyacrylamide gel matrix or agarose gel matrix and nucleotide sequencing. The nucleotide sequencing may be rapidly carried out with an automatic sequencer available from various manufacturers.

As exemplified in Example below, the multiplexing of this invention permits the final amplified products to be free from the background problems as well as non-specificity arising from conventional multiplex processes known in the art.

The advantage of the multiplex amplification is that numerous diseases or specific nucleotide sequence alterations (e.g., single nucleotide polymorphism or point mutation) can be assayed in the same reaction. The number of analyses that can be run simultaneously is unlimited; however, the upper limit is probably about 20 and is likely to be dependent on the size difference required for resolution and methods that are available to resolve the amplified product.

The method of the present invention may be applied to the diagnosis of genetic and infectious diseases, gender determination, genetic linkage analysis, and forensic studies.

IV. Application to DNA Sequencing

The improved specificity allows DS oligo to be used in direct sequencing as a primer of solution-phase sequencing (in particular, cycling sequencing) or as a probe of solid-phase sequencing (in particular, oligonucleotide chip sequencing) by using the principle of the template-dependent extension of DS oligo.

In still further aspect of this invention, there is provided a method for sequencing a target nucleic acid molecule using a dual specificity oligonucleotide from a DNA or a mixture of nucleic acids, which comprises the steps of:

(a) synthesizing a complementary nucleic acid molecule to the target nucleic acid molecule to be sequenced by performing at least two cycles of primer annealing, primer extending and denaturing, using the dual specificity oligonucleotide as a sequencing primer; wherein the dual specificity oligonucleotide has three portions in which a 5'-high $T_m$ specificity portion has a hybridizing nucleotide sequence substantially complementary to a site on the target nucleic acid molecule to hybridize therewith, a separation portion comprises at least two universal bases and a 3'-low $T_m$ specificity portion has a hybridizing nucleotide sequence substantially complementary to a site on the target nucleic acid molecule to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the target nucleic acid molecule; wherein annealing in the synthesizing reaction is performed under conditions that annealing solely by the 3'-low $T_m$ specificity portion does not occur; and (b) determining a nucleotide sequence of the synthesized complementary nucleic acid molecule.

Generally, DNA sequencing has been carried out by various methodologies such as Maxam-Gilbert sequencing, Sanger sequencing, pyrosequencing, and exonuclease digestion sequencing. The present sequencing method intends to improve the pyrosequencing as well as thermal cycle sequencing.

The present method can be performed in accordance with variations of Sanger dideoxy method. Thermal cycle sequencing of the present invention can be done on PCR amplified nucleic acid templates. In addition, according to the invention, thermal cycle sequencing will be performed on a nucleic acid template which has not been PCR amplified just prior to sequencing.

In brief, Sanger sequencing is based on the principle that DNA polymerase will incorporate 2',3'-dideoxynucleotides into nucleic acid chains resulting in chain termination (Sanger et al., (1977) *PNAS. USA* 74:5463). The method developed by Sanger is referred to as the dideoxy chain termination method. In the most traditional one of this method, a DNA segment for which the sequence is desired is cloned into a single-stranded DNA phage, such as M13. These phage DNAs can serve as templates for the primed synthesis of the complementary strand by the Klenow fragment of DNA polymerase I. The primer is a synthetic oligonucleotide to hybridize specifically with a region of the M13 vector near the 3' end of the cloned insert. In each of four sequencing reactions, the primed synthesis is carried out in the presence of sufficient dideoxy analog of one of the four possible deoxynucleotides, in order that the growing chains are randomly terminated by the incorporation of these dead-end nucleotides. The relative concentration of dideoxy to deoxy forms is adjusted to give a spread of termination events corresponding to all the possible chain lengths that can be resolved by gel electrophoresis. Tags incorporated in the growing chains are used to develop an autoradiogram image of the pattern of the DNA in each electrophoresis track. The sequence of the deoxynucleotides in the cloned nucleic acid template is determined from an examination of the pattern of bands in the four lanes As a variation of Sanger method, thermal cycle sequencing method normally involves the use of solutions containing a nucleic acid sequencing primer, deoxynucleoside triphosphates, one or more dideoxynucleoside triphosphates (ddNTPs), a suitable buffer solution, a thermal stable DNA polymerase (e.g., Taq polymerase), and the nucleic acid template to be sequenced. The details of thermal cycle sequencing may be found in U.S. Pat. Nos. 5,432,065, 5,723,298, 5,756,285, 5,817,797 and 5,831,065, the teachings of which are incorporated herein by references in their entity. The processes of the method are generally performed under thermal cycling conditions similar to common PCR.

Once a sequencing reaction has been performed on a nucleic acid template, the determination of the sequence of the molecule requires that the reaction products be identified. A considerable number of detection methods are known in the art. These methods generally involve the detection of tags including radionucleotide, fluorescent, infrared and chemiluminescent labels as described in Ausubel, F. M. et al., *Current Protocols in Molecular Biology*, (1993) John Wiley & Sons, Inc., New York, N.Y. The labels may be tagged with primers or ddNTP, preferably, ddNTP. The most preferred label is fluorescent one including 6-carboxyfluorescein, 6-carboxy-X-rhodamine, 3-(ε-carboxypentyl)-3'-ethyl-5,5'-dimethyloxacarbocyanine, 6-carboxy-X-rhodamine, 4,4-difluoro-4-bora-3α,4α-diaza-s-indacene-3-propionic acid derivatives, and 4,7-dichlororhodamine dyes.

Preferably, the annealing temperature ranges from about 40° C. to 70° C., more preferably, 45° C. to 68° C., and most preferably, 50° C. to 65° C.

The present method proves a high specific sequencing of a target nucleic acid molecule as demonstrated in Example hereunder. More specifically, the mouse placenta-specific homeobox family genes, Psx1 and Psx2 can be differentially sequenced using their sequencing primer designed to have a unique structure of the DS oligo. Such differential sequencing is highlighted in the senses that the overall sequences of the sequencing primers are different in only one base in the 3'-low $T_m$ specificity portion.

Surprisingly, the present invention permits a target nucleic acid molecule contained in a genomic DNA or a population of cDNAs to be directly sequenced without purification or isolation. The success in direct sequencing of a target nucleic acid molecule in a genomic DNA or a population of cDNAs has not yet been reported. Where the present sequencing method is employed to directly sequence a target nucleic acid molecule contained in a population of cDNAs from a total RNA, this, method comprises the steps of:

(a) contacting a population of mRNAs with an oligonucleotide dT primer which is hybridized to polyA tail of the mRNAs under conditions sufficient for template driven enzymatic deoxyribonucleic acid synthesis to occur;

(b) reverse transcribing the mRNAs to which the oligonucleotide dT primer hybridizes to produce a population of a first cDNA strands that are complementary to the mRNAs to which the oligonucleotide dT primer hybridizes;

(c) synthesizing a complementary nucleic acid molecule to the first cDNA strand to be sequenced by performing at least two cycles of primer annealing, primer extending and denaturing, using the dual specificity oligonucleotide as a sequencing primer; wherein the dual specificity oligonucleotide has three portions in which a 5'-high $T_m$ specificity portion has a hybridizing nucleotide sequence substantially complementary to a site on the first cDNA strand to hybridize therewith, a separation portion comprises at least two universal bases and a 3'-low $T_m$ specificity portion has a hybridizing nucleotide sequence substantially complementary to a site on the first cDNA strand to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the first cDNA strand; wherein annealing in the synthesizing reaction is performed under conditions that annealing solely by the 3'-low $T_m$ specificity portion does not occur; and (b) determining a nucleotide sequence of the synthesized the first cDNA strand.

V. Application to Detection of Nucleic Acid Molecule with Genetic Diversity

In another aspect of this invention, there is provided a method for detecting a nucleic acid molecule with genetic diversity by a template-dependent extension reaction of a dual specificity oligonucleotide, which comprises the steps of:

(a) annealing the dual specificity oligonucleotide to a template nucleic acid molecule, wherein the dual specificity oligonucleotide has three portions in which a 5'-high $T_m$ specificity portion has a hybridizing nucleotide sequence substantially complementary to a site on the template nucleic acid to hybridize therewith, a separation portion comprises at least two universal bases and a 3'-low $T_m$ specificity portion has a hybridizing nucleotide sequence substantially complementary to a site on the template nucleic acid to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the template nucleic acid, wherein the annealing is performed under conditions that annealing solely by the 3'-low $T_m$ specificity portion does not occur and annealing occurs when the 5'-high $T_m$ specificity portion and/or the 3'-low $T_m$ specificity portion has one or more mismatched bases to its target site; and (b) extending the dual specificity oligonucleotide to synthesize the nucleic acid molecule complementary to the template.

(c) detecting the occurrence of the template-dependent extension of the dual specificity oligonucleotide Since this application using the DS oligo of this invention is carried out in accordance with the present methods for synthesizing nucleic acid sequence previously discussed, the common descriptions between them are omitted in order to avoid the complexity of this specification leading to undue multiplicity.

This application using the DS oligo of the subject invention can provide an improved method for selectively detecting a nucleic acid sequence with genetic diversity by a template-dependent extension reaction involving annealing and extending steps. In particular, the detection of a target nucleic acid sequence with genetic diversity can be achieved by repeating the process of the template-dependent extension reaction in which the annealing and extension steps are followed by denaturation step.

The present invention is based on mismatch tolerance of the DS oligo.

Genetic diversity has been reported for various genomes. This phenomenon has been considered an obstacle to detect a gene or genome of interest without failure. The present invention is directed to provide an approach to overcome such conventional problems by use of the DS oligo with mismatch tolerance. The DS oligo with a defined sequence can be annealed to several target sequences showing genetic diversity and result in successful amplification and detection of nucleotide sequences of interest. In other words, the DS oligo originally developed to dramatically enhance specificity of annealing and hybridization can be also used in processes requiring mismatch tolerance where annealing or stringent conditions are suitably adjusted.

To provide the DS oligo demonstrating mismatch tolerance, it should be designed on the basis of a conserved region of nucleic acid molecules generated by aligning all available nucleotide sequences. The term "conserved region" as used herein refers to a segment of nucleotide sequence of a gene or amino acid sequence of a protein that is significantly similar between various different nucleotide sequences of a gene. This term is interchangeably used with the term "conserved sequence".

In a preferred embodiment, the most conserved sequence within the conserved region is located in the 3'-end portion of the DS oligo and the lowest conserved sequence in the separation portion. The 5'-high $T_m$ specificity portion and/or the 3'-low $T_m$ specificity portion, preferably 5'-high $T_m$ specificity portion may one or more, preferably, one to three, more preferably one or two mismatched bases to its target site due to mismatch tolerance of the DS oligo.

For imposing mismatch tolerance on the DS oligo, the annealing condition, in particular, annealing temperature is important. The annealing is performed under conditions that annealing solely by the 3'-low $T_m$ specificity portion does not occur, yet annealing by all the portions occurs when the 5'-high $T_m$ specificity portion and/or the 3'-low $T_m$ specificity portion has one or more mismatched bases to its target site.

Preferably, the annealing temperature ranges from about 40° C. to 70° C., more preferably, 45° C. to 68° C., and most preferably, 50° C. to 65° C.

According to a preferred embodiment, the present invention is performed in accordance with polymerase chain reaction (PCR).

The detection step of the present method may be carried out by a multitude of conventional techniques. For example, the detection of the product of the template-dependent extension may be readily performed by conventional gel electrophoresis if the preset method is executed in a repeated manner to generate products sufficient to be detected in a gel. If labeled materials including those detectable by spectroscopic measurement, photochemical measurement, biochemical measurement, bioelectronic measurement, immunochemical measurement, electronic measurement, and chemical measurement, a suitable measurement may be performed for detecting the occurrence of the template-dependent extension.

Genetic diversity is most frequently found and generated in viral genome (Nathalie B. et al., (2004) *Journal of Clinical Microbiology*, 42, 3532; Tersa C. et al., (2002) *Journal of Infectious Diseases*, 185, 1660; Takashi E. et al., (2004) *Journal of Clinical Microbiology*, 42, 126; and Elizabeth R. et al., (2001) *Clinical Infectious Diseases*, 32, 1227). In this regard, it is preferred that the nucleic acid molecule with genetic diversity to be detected is a nucleic acid of a virus exhibiting genetic diversity. For example, where the present invention is applied to detect human metapneumoviruses exhibiting genetic diversity by PCR, the most preferable primer set designed to have the structure of the DS oligo is set forth in SEQ ID NOs: 39 (for 5' primer) and 40 (for 3' primer) or SEQ ID NOs: 39 and 41 (for 3' primer).

VI. Application to Detection of Target Nucleotide Sequence Using DS Oligos Immobilized on Microarray This application is a novel process for detecting target nucleotide sequence by repeating the template-dependent reaction on DS oligo-immobilized microarray.

In another aspect of this invention, there is provided a method for detecting a target nucleotide sequence in a nucleic acid sample by a template-dependent extension reaction, comprising the steps of:

(a) extending a dual specificity oligonucleotide as a probe immobilized on a substrate comprising at least one cycle of a hybridization, a template-dependent extension and a denaturation, wherein the hybridization is performed by contacting the dual specificity oligonucleotide to the nucleic acid sample, wherein the dual specificity oligonucleotide has three portions in which a 5'-high $T_m$ specificity portion has a hybridizing nucleotide sequence substantially complementary to a site on the target nucleotide sequence to hybridize therewith, a separation portion comprises at least two universal bases and a 3'-low $T_m$ specificity portion has a hybridizing nucleotide sequence substantially complementary to a site on the target nucleotide sequence to hybridize therewith, $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the target nucleotide sequence, wherein the hybridization is performed under conditions that hybridization solely by the 3'-low $T_m$ specificity portion does not occur; and (b) analyzing the occurrence of the template-dependent extension.

A schematic representation for detecting a target nucleotide sequence in a nucleic acid sample by use of DS oligo-immobilized microarray is illustrated FIG. 4.

This process using the DS oligos may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide and target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

The DS oligos are immobilized on a substrate. A preferable substrate includes suitable solid or semi-solid supporters, such as membrane, filter, chip, slide, wafer, fiber, magnetic or nonmagnetic bead, gel, tubing, plate, macromolecule, microparticle and capillary tube. Such immobilization may occur through chemical binding or covalent binding by ultra-violet radiation. In an embodiment of this invention, the DS oligos are bound to a glass surface modified to contain epoxy compounds or aldehyde groups or to a polylysin-coated surface. Furthermore, the DS oligos are bound to a substrate through linkers (e.g. ethylene glycol oligomer and diamine). Immobilized DS oligos may be fabricated to produce array or arrays for a given application by conventional fabrication technologies such as photolithography, ink-jetting, mechanical microspotting, and derivatives thereof.

According to the present method, dNTPs used in the extension step are preferably labeled. For labeling, materials detectable by spectroscopic measurement, photochemical measurement, biochemical measurement, bioelectronic measurement, immunochemical measurement, electronic measurement, or chemical measurement are used. For instance, the labels include, yet are not limited to, radioisotopes like $P^{32}$ and $S^{35}$, chemiluminescent compounds, spectroscopic markers, such as fluorescence markers and dyes, and magnetic labels. The dyes, for example, include, but not limited to, quinoline dye, triarylmethane dye, phthalein, azo dye, and cyanine dye. The fluorescence makers include, but not limited to, fluorescein, phycoerythrin, rhodamine, lissamine, Cy3 and Cy5 (Pharmacia). Labeling is performed according to various methods known in the art.

Target nucleotide sequences in a nucleic acid sample are hybridized with the DS oligos as probes immobilized in a substrate, preferably, a solid support, and in turn the DS oligos hybridized with target nucleotide sequences are extended using dNTPs, preferably fluorescence-labeled dNTPs and DNA polymerase in a template-dependent fashion. The step (a) is preferably repeated to perform hybridization reactions to the extent that all or most of the DS oligos are hybridized with target nucleotide sequences, making the results of hybridization analysis more reproducible.

The occurrence of hybridization is verified with various methods known in the art depending on the types of labels used. For example, fluorescence microscope, preferably, confocal fluorescence microscope is used for fluorescence labels, and the intensity of the signal detected with such instruments increases proportionally to the extent of hybridization. Fluorescence microscopes, in general, are equipped with a scanning device which builds up a quantitative two dimensional image of hybridization intensity. The intensity of the signal detected with such instruments increases proportionally to the extent of hybridization and then the extent of a template-dependent extension.

The present invention will now be described in further detail by examples. It would be obvious to those skilled in the art that these examples are intended to be more concretely illustrative and the scope of the present invention as set forth in the appended claims is not limited to or by the examples.

Example 1

PCR Specificity Using Dual Specificity (DS) Oligonucleotides

The DS oligonucleotides developed by the present invention were applied as primers to amplify target nucleotide sequences of mouse cytokine family genes IL-19 and IL-1beta. The process and results for the amplification of the target nucleotide sequences of IL-19 and IL-1beta using DS primers are described herein.

The following conventional primer sequences were chosen and used for comparing to DS oligonucleotides in view of PCR specificity:

The IL-19-specific conventional primers used in the Example (500 bp) are:

```
IL19-5'-0
                                      (SEQ ID NO: 1)
5'-GTCTCATCTGCTGCCCTTAAGTCTCTAGGAGAACT-3';
and IL19-3'-0
                                      (SEQ ID NO: 2)
5'-CATAGGCCTGGAAGAAGCCGCTTTACAATAAGTTAG-3'.
```

The IL-1beta-specific conventional primers used in the Example (550 bp) are:

```
IL1b-5'-0
                                      (SEQ ID NO: 3)
5'-GGAGAGTGTGGATCCCAAGCAATACCCAAAGAAG-3';
and IL1b-3'-0
                                      (SEQ ID NO: 4)
5'-AGACCTCAGTGCAGGCTATGACCAATTCATCCC-3'.
```

The DS oligonucleotides of the subject invention were applied to these conventional primer sequences to demonstrate whether the DS oligonucleotides can overcome the main problems arising from these conventional primer sequences, such as generation of background and non-specific products.

The following DS primers comprise sequences identical to the above conventional primers except the separation portion having a polydeoxyinosine [poly(dI)] linker between the 5' portion and the 3' portion. The DS primers are designed to comprise a 5'-high $T_m$ specificity portion and a 3'-low $T_m$ specificity portion in a way that $T_m$ of the 5'-high $T_m$ specificity portion is higher than that of the 3'-low $T_m$ specificity portion, while the separation portion has the lowest $T_m$ among the three portions.

The DS primers for IL-19 used in the Example (500 bp) are:

```
IL19-5'
                                      (SEQ ID NO: 5)
5'-GTCTCATCTGCTGCCCTTAAIIIIITAGGAGAACT-3';
and 1L19-3'
                                      (SEQ ID NO: 6)
5'-CATAGGCCTGGAAGAAGCCGIIIIICAATAAGTTAG-3',
``` wherein I is deoxyinosine.

The DS primers for IL-1beta used in the Example (550 bp) are:
IL1b-5'   5'-GGAGAGTGTGGATCCCAAGCIIIIIC-CAAAGAAG-3' (SEQ ID NO:7); and IL1b-3' 5'-AGACCTCAGTGCAGGCTATGIIIIIT-TCATCCC-3' (SEQ ID NO:8), wherein I is deoxyinosine.

The target PCR amplification was conducted in the final volume of 20 μl containing 2 μl (50 ng) of the genomic DNA isolated from placenta tissues of mouse strain ICR, 2 μl of 10×PCR reaction buffer containing 15 mM MgCl$_2$ (Roche), 2 μl of dNTP (2 mM each dATP, dCTP, dGTP and dTTP), 1 μl of 5' DS or conventional primer (10 μM), 1 μl of 3' DS or conventional primer (10 μM), and 0.5 μl of Taq polymerase (5 units/μl; Roche); the tube containing the reaction mixture was placed in a preheated (94° C.) thermal cycler; samples were denatured for 5 min at 94° C. and subjected to 30 cycles of 1 min at 94° C., 1 min at 60° C., and 1 min at 72° C., followed by a 7-min incubation at 72° C.

The amplified products were analyzed by electrophoresis in a 2% agarose gel and were detected by staining with ethidium bromide. The resulting PCR products could be also detected on a denaturing polyacrylamide gel by autoradiography or non-radioactive detection methods, such as silver staining (Gottschlich et al., (1997) *Res. Commun. Mol. Path. Pharm.* 97, 237-240; Kociok, N., et al. (1998) *Mol. Biotechnol.* 9, 25-33), or by using fluorescent-labelled oligonucleotides (Bauer D., et al., (1993) *Nucleic Acids Res.* 21, 4272-4280; Ito, T. et al., (1994) *FEBS Lett.* 351, 231-236. Luehrsen, K. R. et al., (1997) *BioTechniques* 22, 168-174; Smith, N. R. et al., (1997) *BioTechniques* 23, 274-279), and the use of biotinylated primers (Korn, B. et al., (1992) *Hum. Mol. Genet.* 1, 235-242; Tagle, D. A. et al., (1993) *Nature* 361. 751-753; Rosok, O. et al., (1996) *BioTechniques* 21, 114-121).

Figure 5:
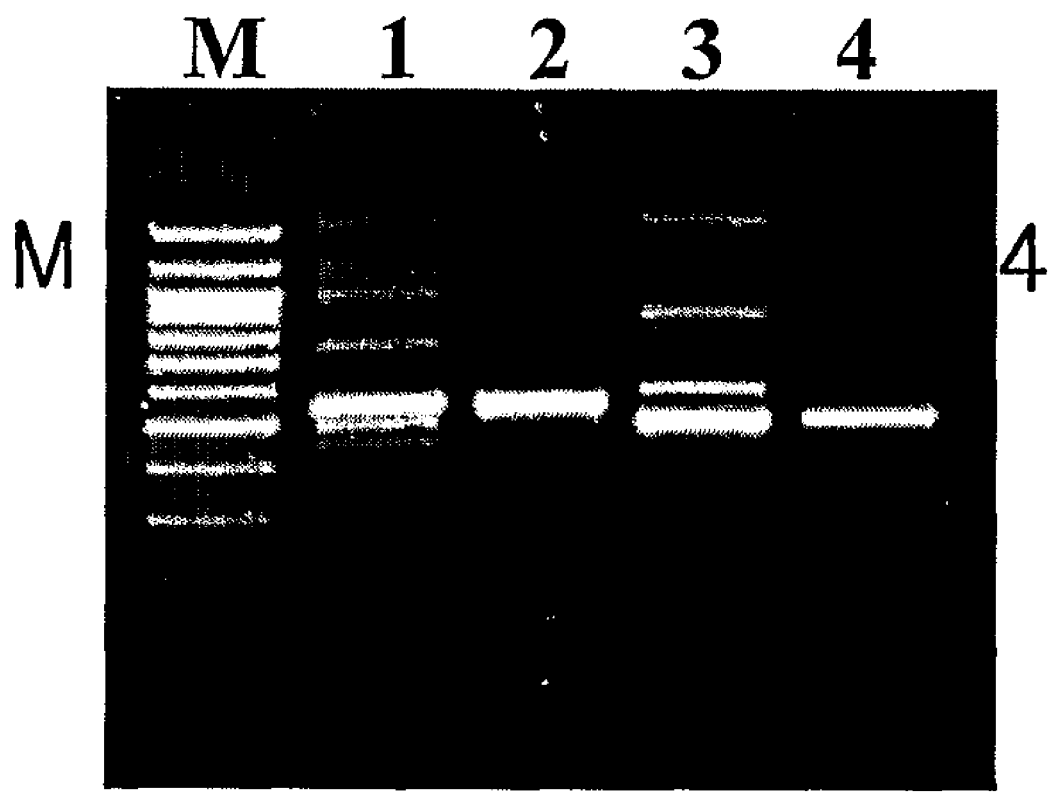
FIG. 5 is an agarose gel photograph showing the results of PCR amplification for cytokine family genes, IL-1β and IL-19, using a set of conventional primers (IL-1b-5'-0 and IL-1b-3'-0, lane 1; IL-19-5'-0 and IL-19-3'-0, lane 3) and the dual specificity oligonucleotides (IL-1b-5' and IL-1b-3', lane 2; IL-19-5' and IL-19-3', lane 4). M is a 100-bp size marker generated by Forever 100-bp Ladder Personalizer (Seegene, Inc. Seoul, Korea).

As shown in FIG. 5, the target PCR amplifications for cytokine family genes IL-1b and IL-19 using each primer set of IL1b-5' and IL1b-3', and IL19-5' and IL 19-3' generate a single band which corresponds to the expected size of 550-bp for IL-1beta (lane 2) and the expected size of 500-bp for IL-19 (lane 4), respectively. Subsequent cloning and sequence analysis of the clones confirmed that the bands are IL-1beta and IL-19 fragments. In contrast, the conventional primer sets (IL19-5'-0 and IL19-3'-0; IL1b-5'-0 and IL1b-3'-0), which do not contain the [poly(dI)], produced non-specific products (FIG. 5, lanes 1 and 3). These results indicate that the DS primers designed to have three different $T_m$ portions (5'-high $T_m$ specificity portion, 3'-low $T_m$ specificity portion and separation portion) can overcome the main problems arising from the conventional primer sequences such as background and non-specific products and enhance PCR specificity remarkably.

Example 2

Evaluation of PCR Specificity Using Dual Specificity (DS) Oligonucleotides

The dual specificity oligonucleotides are characterized by high hybridization specificity and mismatch tolerance arising from their unique structure, depending on hybridization stringency. High hybridization specificity of the DS oligonucleotides is achieved under high stringency conditions that both 5'- and 3'-portions are annealed to the template. Meanwhile, mismatch tolerance of the DS oligonucleotides is achieved under stringency conditions that both 5'- and 3'-portions are annealed to the template despite the presence of one or more, yet limited, base pair mismatches.

The dual specificity of DS oligonucleotides developed according to the present invention was evaluated in terms of hybridization specificity and mismatch tolerance by the 3'-RACE of a novel gene, DEG10, which was identified to be expressed in mouse placenta (Kim, Y. J. et al., (2004) Annealing control primer system for identification of differentially expressed genes on agarose gels. BioTechniques 36:424-434; XM_129567). For this evaluation, a few nucleotides in both portions were replaced with other nucleotides as to be mismatched to the target template sequence.

The 5'-DEG10-specific DS primers used in the Example are:

```
DEG10-5'-108:
                                      (SEQ ID NO: 9)
5'-TGTAGTTTTGGGTTTCCTCCIIIIICTCCGATG-3';

DEG10-5'-103:
                                      (SEQ ID NO: 10)
5'-TGTAGTTTTGGGTTTCCTCCIIIIICTGCCATC-3';

DEG10-5'-102:
                                      (SEQ ID NO: 11)
5'-TGTAGTTTTGGGTTTCCTCCIIIIICTCCCATC-3';

DEG10-5'-101:
                                      (SEQ ID NO: 12)
5'-TGTAGTTTTGGGTTTCCTCCIIIIICTCCCATG-3';

DEG10-5'-158:
                                      (SEQ ID NO: 13)
5'-TGTACTTATGCGTATCGTCCIIIIICTCCGATG-3';

DEG10-5'-138:
                                      (SEQ ID NO: 14)
5'-TGTACTTTTGCGTTTCGTCCIIIIICTCCGATG-3';
and DEG10-5'-128:
                                      (SEQ ID NO: 15)
5'-TGTAGTTATGGGTATCCTCCIIIIICTCCGATG-3',
``` wherein the replaced nucleotides are underlined and bold and I is deoxyinosine.

A. Enhancement in PCR Specificity Under High Stringency

Total RNAs from 17.5-dpc (E17.5) placenta tissues of mouse strain ICR were isolated and used for the synthesis of first-strand cDNAs by reverse transcriptase, as described previously (Hwang, I. T., et al., (2003) Annealing control primer system for improving specificity of PCR amplification. *BioTechniques* 35:1180-1184). Reverse transcription reaction was performed using the total RNAs for 1.5 hr at 42° C. in a reaction volume of 20 μl composed of the following: 3 μg of total RNA, 4 μl of 5× reaction buffer (Promega, USA), 5 μl of dNTPs (each 2 mM), 2 μl of 10 μM cDNA synthesis primer (oligo (dT)$_{20}$-Adaptor), 0.5 μl of RNase inhibitor (40 units/μl, Promega), and 1 μl of reverse transcriptase (200 units/μl, Promega). First-strand cDNAs were diluted by adding 180 μl of ultra-purified H$_2$O. The cDNA synthesis primer oligo (dT)$_{18}$-ACP1 is: 5'-CTGTGAATGCTGCGACTACGATIIIII (T)$_{18}$-3', wherein I is deoxyinosine.

The 3'-RACE of DEG10 was conducted in a final volume of 20 μl containing 2 μl (30 ng) of the diluted first strand cDNA, 2 μl of 10×PCR reaction buffer containing 15 mM MgCl$_2$ (Roche), 2 μl of dNTP (2 mM each dATP, dCTP, dGTP, dTTP), 1 μl of one of DEG10-specific DS primers (10 μM), 1 μl of oligo (dT)$_{15}$-ACP2 (10 μM), and 0.5 μl of Taq polymerase (5 units/μl; Roche); the tube containing the reaction mixture was placed in a preheated (94° C.) thermal cycler; samples were denatured for 5 min at 94° C. and subjected to 30 cycles of 1 min at 94° C., 1 min at 68° C., and 1 min at 72° C., followed by a 7-min incubation at 72° C. The oligo (dT)$_{15}$-ACP2 is: 5'-CTGTGAATGCTGCGACTAC-GATIIIII(T)$_{15}$-3', wherein I is deoxyinosine.

B. Mismatch Tolerance of DS Oligonucleotides

The sample DS primers, template, and PCR conditions for the 3'-RACE of DEG10 used in the Example 2A were employed except for the annealing temperature. PCR amplification was conducted under the following conditions: one cycle of 94° C. for 5 min, 60° C. for 3 min, and 72° C. for 3 min; followed by 29 cycles of 94° C. for 40 s, 65° C. for 1 min, and 72° C. for 40 s, and a 7-min final extension cycle at 72° C.

As a result, FIG. 6A shows the high hybridization specificity of DS oligonucleotide primers by the 3'-RACE of DEG10. The intact 5'-DEG10-specific DS primer (DEG10-5'-108) generated an expected 677-bp product of the DEG10 3'-RACE (lane 1). In contrast, the other primers (DEG10-5'-103, DEG10-5'-102, DEG10-5'-101, DEG10-5'-158, DEG10-5'-138, and DEG10-5'-128) with mismatched sequences at the 5' portion or the 3' portion did not generate any product: the mismatch of three (lane 2), two (lane 3), or one (lane 4) base(s) at the 3' portion; the mismatch of five (lane 5), three (lane 6), or two (lane 7) base(s) at the 5' portion.

These results demonstrate that the dual specificity of the DS primers can discriminate the mismatched bases not only at the 3'-end but also at the 5'-end under such high stringency conditions.

In general, the region of primers that should be perfectly complementary to the template is the 3'-end, because this end is the region extended by DNA polymerase and is therefore the most important for ensuring annealing to the correct target sequence to occur. Meanwhile, the 5'-end of primers is less important in determining the specificity of annealing to the target sequence and can be modified to carry additional sequence such as restriction sites and promoter sequences that are not complementary to the template (McPherson, M. J., Moller, S. G. (2000) PCR. BIOS Scientific Publishers, Springer-Verlag New York Berlin Heidelberg, N.Y.). In contrast to these, the exceptional advantage of the DS primers is demonstrated by the dual specificity due to their unique structure, allowing discrimination of mismatched bases in 5'-end as well as in 3'-end.

Figure 6B:
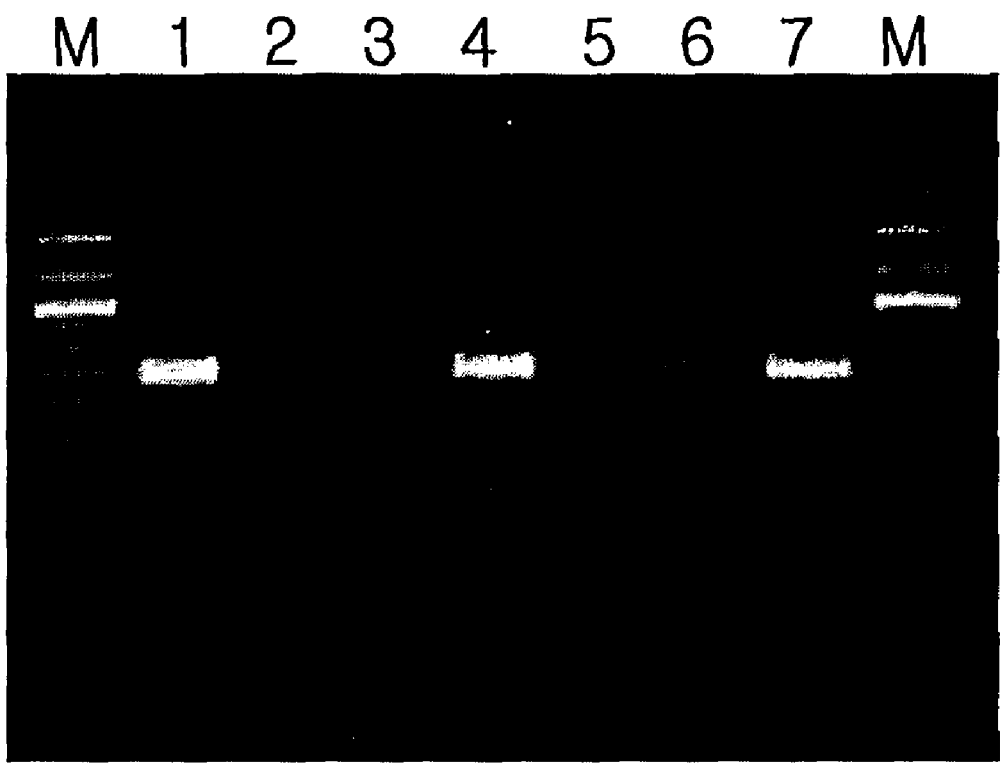
FIG. 6B is an agarose gel photograph showing the results of the 3'-RACE of the DEG 10 gene, demonstrating the mismatch tolerance of the dual specificity oligonucleotide in PCR. Lane 1 represents a primer with perfect match sequence, lanes 2-4 represent primers with 3, 2 and 1 base mismatch at its 3'-low $T_m$ specificity portion, respectively, and lanes 5-7 represent primers with 5, 3 and 2 base mismatch at its 5'-high $T_m$ specificity portion, respectively. M is a 100-bp size marker generated by Forever 100-bp Ladder Personalizer.

FIG. 6B shows an example of the mismatch tolerance of DS oligonucleotide primers by the 3'-RACE of DEG10. Although the DS primers (DEG10-5'-108, DEG10-5'-101, DEG10-5'-128, and DEG10-5'-138) having no or a few mismatch nucleotides at their 5'- or 3'-end portions still generated an expected 677 bp product of the DEG10 3'-RACE (lanes 1, 4, 6 and 7). In contrast, the other primers (DEG10-5'-103, DEG10-5'-102, and DEG10-5'-158) with more mismatched nucleotides at their 5' or 3' portions did not generate any product (lanes 2, 3 and 5). These results indicate that the DS primers can be also applied to amplifications of diverse nucleotide sequences requiring mismatch tolerance.

In summary, these results support the following principles of DS primers:

1) only when annealing occurs by both 5'-high $T_m$ specificity portion and 3'-low $T_m$ specificity portions, the DS primer is extended to synthesize a nucleic acid molecule complementary to the template (lane 1); however, 2) when annealing occurs only by the 5'-high $T_m$ specificity portion and not by the 3'-low $T_m$ specificity portion, the DS primer is not extended to synthesize a nucleic acid molecule complementary to the template (lanes 2-4); and 3) even though the sequence of the 3'-low $T_m$ specificity portion has a perfect match to the template, the annealing solely by the 3'-low $T_m$ specificity portion does not occur under high stringent conditions (lanes 5-7). Regarding to the annealing portion, the DS primer is distinctly different from the annealing control primer (ACP) that is extended only by annealing of the 3'-end portion in an initial PCR step (Hwang, I. T., et al., (2003) Annealing control primer system for improving specificity of PCR amplification. *BioTechniques* 35:1180-1184).

Example 3

Single-Base Discrimination Using Dual Specificity (DS) Oligonucleotides

To demonstrate the dual specificity of DS oligonucleotides for single-base discrimination, the mouse placenta-specific homeobox family genes Psx1 and Psx2 cDNAs were amplified with either conventional primers or DS primers. Overall sequence identity between the two Psx cDNAs was 91% at the nucleotide level (Han, Y. J., et al., (2000) Identification and characterization of Psx2, a novel member of the Psx (placenta-specific homeobox) family. *Gene* 241:149-155). The 5'-primers were designed to distinguish Psx1 and Psx2 by one- or two-base discrimination (FIG. 7A). However, the 3'-primer was designed to have a conserved sequence for both Psx cDNAs. The Psx1- and Psx2-specific conventional and DS primer sequences are:

```
Psx1-5'-10:
                                        (SEQ ID NO: 16)
5'-AAGGAAGACATGCTGGTGATGGTGCTTCTAGCT-3';

Psx2-5'-10:
                                        (SEQ ID NO: 17)
5'-AAGGAAGACATGCTGGTGATGGTGCTTCTGGCC-3';

Psx1-5'-11:
                                        (SEQ ID NO: 18)
5'-AAGGAAGACATGCTGGTGATIIIIIITTCTAGCT-3';

Psx2-5'-11:
                                        (SEQ ID NO: 19)
5'-AAGGAAGACATGCTGGTGATIIIIIITTCTGGCC-3';

Psx1-5'-40:
                                        (SEQ ID NO: 20)
5'-TCTTGCACGATGGATGGGTGTGGATGAATGTGA-3';

Psx2-5'-40:
                                        (SEQ ID NO: 21)
5'-TCTTGCACGATGGATGGGTGTGGATGAATCTGA-3';

Psx1-5'-41:
                                        (SEQ ID NO: 22)
5'-TCTTGCACGATGGATGGGTGIIIIIGAAIGIGA-3';

Psx2-5'-41:
                                        (SEQ ID NO: 23)
5'-TCTTGCACGATGGATGGGTGIIIIIGAAICIGA-3';
and Psx-3'-2:
                                        (SEQ ID NO: 24)
5'-TTCATCCACACCCATCCATCIIIIIAGATCCCT-3',
``` wherein the Psx1- or Psx2-specific nucleotides are underlined and bold.

A. First-Strand cDNA Synthesis

The mouse placenta first-strand cDNA synthesized in Example 2 was used as a starting material for 3'-RACE and a target PCR of Psx cDNA.

B. 3'-RACE of Psx1 and Psx2 Using Psx1- and Psx2-Specific DS Primer

The 3'-RACE of Psx1 and Psx2 were conducted in a final volume of 20 µl containing 2 µl (30 ng) of the diluted first strand cDNA, 2 µl of 10×PCR reaction buffer containing 15 mM MgCl$_2$ (Roche), 2 µl of dNTP (2 mM each dATP, dCTP, dGTP and dTTP), 1 µl of one of 5'-Psx1- or 5'-Psx2-specific DS or conventional primers (10 µM), 1 µl of oligo (dT)$_{15}$-ACP2 (10 µM), and 0.5 µl of Taq polymerase (5 units/µl; Roche); the tube containing the reaction mixture was placed in a preheated (94° C.) thermal cycler; samples were denatured for 5 min at 94° C. and subjected to 30 cycles of 1 min at 94° C., 1 min at 60-65° C., and 1 min at 72° C., followed by a 7-min incubation at 72° C.

C. Target Nucleic Acid Amplification of Psx1 and Psx2 Using Psx1- and Psx2-Specific DS Primers The target PCR amplification of Psx1 and Psx2 were conducted in a final volume of 20 fit containing 2 μl (30 ng) of the diluted first strand cDNA, 2 μl of 10×PCR reaction buffer containing 15 mM MgCl$_2$ (Roche), 2 μl of dNTP (2 mM each dATP, dCTP, dGTP and dTTP), 1 μl of one of 5'-Psx1- or 5'-Psx2-specific DS or conventional primers (10 mM), 1 μl of Psx-3'-2 (10 μM), and 0.5 μl of Taq polymerase (5 units/μl; Roche); the tube containing the reaction mixture was placed in a preheated (94° C.) thermal cycler; samples were denatured for 5 min at 94° C. and subjected to 30 cycles of 1 min at 94° C., 1 min at 60-65° C., and 1 min at 72° C., followed by a 7-min incubation at 72° C.

Figure 7B:
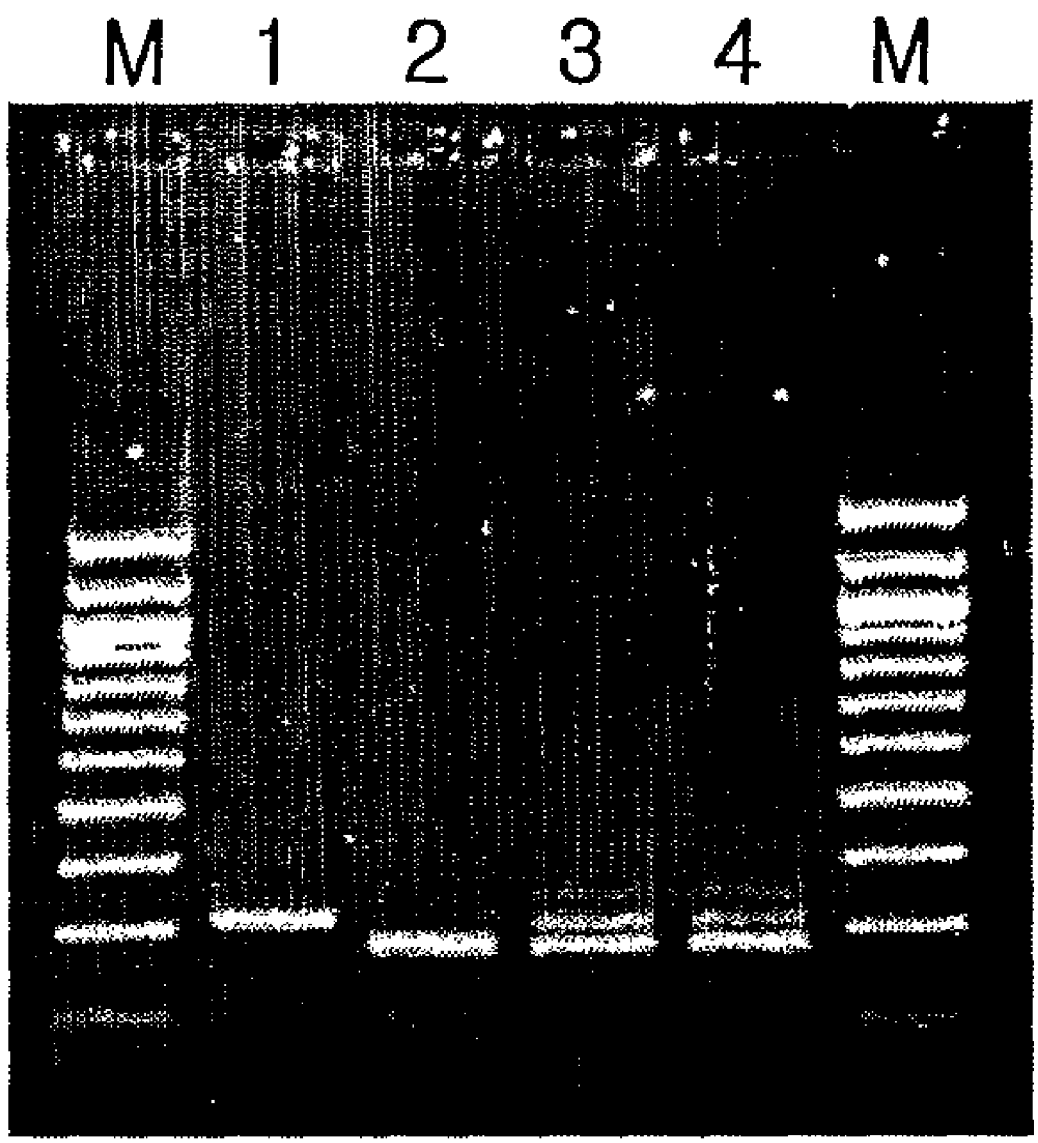
FIG. 7B is an agarose gel photograph showing the results of the 3'-RACE of Psx1 and Psx2. Lane 1,3'-RACE of Psx1 using the dual specificity oligonucleotide primer Psx1-5'-41; Lane 2,3'-RACE of Psx2 using the dual specificity oligonucleotide primer Psx2-5'-41; Lane 3, 3'-RACE of Psx1 using conventional primer Psx1-5'-40; and Lane 4,3'-RACE of Psx2 using conventional primer Psx2-5'-40. M is a 100-bp size marker generated by Forever 100-bp Ladder Personalizer.

As a result, FIG. 7B shows the products of the 3'-RACE and target PCR generated by 5'-Psx1- or -Psx2-specific primers. Since the two Psx cDNAs differ from each other by 29-bp deletion or insertion toward their 3'-end, the products different in size by 29-bp are expected to be amplified by their 3'-RACE. The 3'-RACE of Psx1 cDNA using the Psx1- or Psx2-specific DS primers Psx1-5'-41 and Psx2-5'-41 each generated a single band which corresponds to the expected size 311-bp (lane 1) and 282-bp (lane 2), respectively. Subsequent sequence analysis of the products generated by the 3'-RACE confirmed that the 5'-Psx1- and -Psx2-specific primers amplified Psx1 and Psx2 cDNAs, respectively. In contrast, the conventional primers (Psx1-5'-40 and Psx2-5'-40), which do not comply with the principles of DC oligonucleotides, did not distinguish two Psx cDNAs (lanes 3 and 4).

These results indicate that the DS primers according to the present invention can discriminate a single-base mismatch. Therefore, DS oligonucleotides can be applied for identifying point mutations or single nucleotide polymorphism genotyping.

Example 4

Direct Sequencing of a Target cDNA from cDNA Pool Using Dual Specificity (DS) Oligonucleotides Most attempts to identify and isolate a novel cDNA result in the acquisition of clones that represent only a part of the mRNA's sequence. Once the partial sequence has been identified, the remainder of the transcript can be often obtained through either typical cDNA library screening or PCR-based methods such as RACE (rapid amplification of cDNA ends), followed by the sequencing of the obtained cDNA. Thus, all current methods are a prerequisite step for obtaining the sequence information of the remainder of the transcript. If the missing sequence information is directly obtained from a population of cDNAs generated from a target cell, these time-consuming prerequisite steps can be completely bypassed and the sequence of the target cDNA can be determined directly from a crude biological sample.

The DS oligonucleotides of the subject invention were applied as primers to directly sequence mouse placenta-specific homeobox gene Psx cDNAs using placenta first-strand cDNA pool. The process and results for direct sequencing of the placenta-specific gene cDNAs from placenta cDNA pool are described herein. The same 5'-Psx-specific DS primers used in Example 3 were used. They are Psx1-5'-11, Psx2-5'-11, Psx1-5'-41, and Psx2-5'-41.

A. First-Strand cDNA Synthesis

The mouse placenta first-strand cDNA synthesized in Example 2 was used as a template for direct sequencing of Psx cDNAs.

B. Direct Sequencing of Psx cDNA from Placenta cDNA Pool Using Psx Specificity DS Primer The cycle sequencing reaction were conducted in a final volume of 20 μl containing 13 μl (150 ng) of the diluted first strand cDNA, 2 μl of ABI PRISM Big Dye Terminator Reaction mix (Applied Biosystems, USA), 3 μl of 5× sequence reaction buffer (Applied Biosystems), and 1.6 μl of one of 5'-Psx1- or 5'-Psx2-specific DS primers (1 μM); the tube containing the reaction mixture was placed in a preheated (94° C.) thermal cycler; samples were denatured for 5 min at 94° C. and subjected to 40-50 cycles of 10 sec at 94° C., 3 min at 50-60° C., and 4 min at 60-65° C. The sequencing products were purified as the following: 1) add 2 μl of 3 M sodium acetate (pH 4.6) and 50 μl of fresh cold 100% EtOH, 2) keep at −75° C. for 30 min, 3) centrifuge for 15-30 min at 13,000 g and remove the supernatant, 4) wash with 200 μl of 70% EtOH, 5) centrifuge for 15-30 min at 13,000 g and remove the supernatant carefully, and dry. The pellet was re-suspended in 10 μl of HiDi Formamide just before running the sequencing product into ABI PRISM 3100 Genetic Analyzer.

Figure 8:
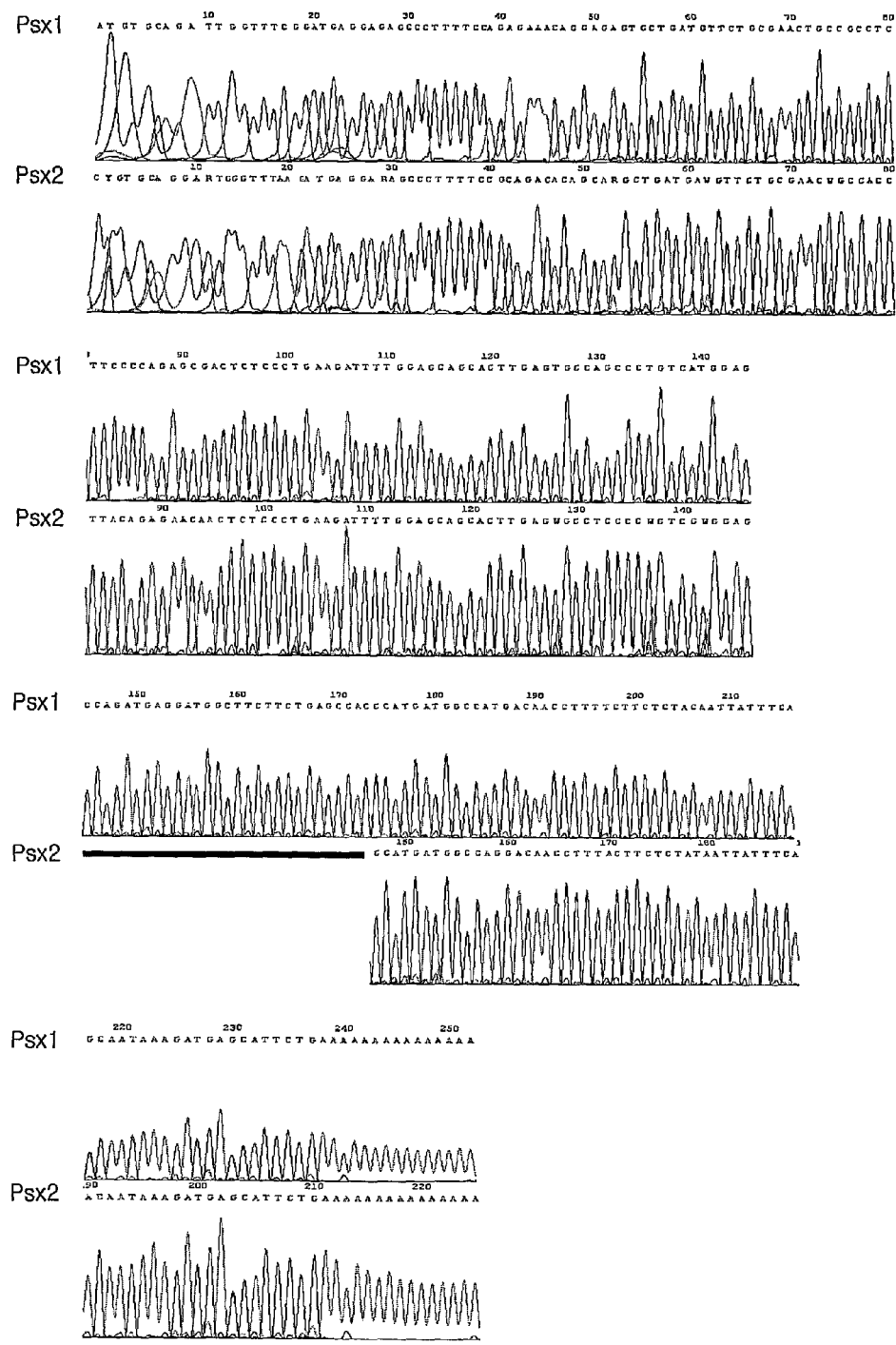
FIG. 8 shows the results of direct cycling sequencing for Psx1 and Psx2 genes from mouse placenta cDNA pool using the dual specificity oligonucleotide primers Psx1-5'-41 (for Psx1) and Psx2-5'-41 (for Psx2) as a sequencing primer.

Surprisingly, the Psx DS primers precisely sequenced their-specific Psx cDNAs. In other words, Psx1-specific DS primer (Psx1-5'-41) sequenced only Psx1 cDNA and Psx2-specific DS primer (Psx2-5'-41) sequenced only Psx2 cDNA (FIG. 8). The 29-bp deletion region in Psx2 is shown by a black bar. In contrast, the conventional primers (Psx1-5'-40 and Psx2-5'-40), which do not comply with the principles of DS oligonucleotides, did not distinguish two Psx cDNAs.

These results indicate that DS primers can discriminate single-base mismatch even in cycle sequencing as well as in PCR amplification.

Example 5

Multiplex PCR Using Dual Specificity (DS) Oligonucleotides

To demonstrate the application of DS oligonucleotide primers in multiplex PCR, nine different cytokine family genes were amplified with DS primers. The process and results for the multiplex PCR amplification using DS primers are described herein. The cytokine family gene-specific DS primers were designed to generate a 50 bp ladder by using the longest exon sequence of each cytokine gene.

The DS primers for EL-3 used in the Example (200 bp) are:

```
                                            (SEQ ID NO: 25)
IL3-5'   5'-GCTGCCAGGGGTCTTCATTCIIIIICTGGATGA-3';
and (SEQ ID NO: 26)
IL3-3'   5'-GGCCATGAGGAACATTCAGAIIIIIGGTGCTCT-3'.
```

The DS primers for IL-15 used in the Example (250 bp) are:

```
                                            (SEQ ID NO: 27)
IL15-5'  5'-ATGTAGCAGAATCTGGCTGCIIIIIATGTGAGG-3';
and (SEQ ID NO: 28)
IL15-3'  5'-ATGTGATCCAAGTGGCTCATIIIIICCTTGTTAGG-3'.
```

The DS primers for IL-18 used in the Example (300 bp) are:

```
IL18-5'
                                        (SEQ ID NO: 29)
5'-AGGAAATGGATCCACCTGAAAIIIIITGATGATATA-3';
and IL18-3'
                                        (SEQ ID NO: 30)
5'-ATGGAAATACAGGCGAGGTCIIIIIAAGGCGCA-3'.
```

The DS primers for IL-25 used in the Example (350 bp) are:

```
                                        (SEQ ID NO: 31)
IL25-5' 5'-AGCTCTCCAAGCTGGTGATCIIIIICAAGGCGG-3';
and (SEQ ID NO: 32)
IL25-3' 5'-GAGCTGCCCTGGATGGGGTTIIIIIGTGGTCCT-3'.
```

The DS primers for IL-2 used in the Example (400 bp) are:

```
                                        (SEQ ID NO: 33)
IL2-5' 5'-CTCTGACAACACATTTGAGTGCIIIIICGATGATGAG-3';
and (SEQ ID NO: 34)
IL2-3' 5'-GTGCTGTCCTAAAAATGACAGAIIIIIGAGCTTATTT-3'.
```

The DS primers for IL-6 used in the Example (450 bp) are:

```
IL6-5'
                                        (SEQ ID NO: 35)
5'-CCAATGCTCTCCTAACAGATAAIIIIIAGTCACAGAA-3';
and IL6-3'
                                        (SEQ ID NO: 36)
5'-AGGTAAACTTATACATTCCAAGAAAIIIIITGGCTAGG-3'.
```

The DS primers for IL-19 used in the Example (500 bp) are:

```
IL19-5'
                                        (SEQ ID NO: 5)
5'-GTCTCATCTGCTGCCCTTAAIIIIITAGGAGAACT-3';
and IL19-3'
                                        (SEQ ID NO: 6)
5'-CATAGGCCTGGAAGAAGCCGIIIIICAATAAGTTAG-3'.
```

The DS primers for IL-1beta used in the Example (550 bp) are:

```
                                        (SEQ ID NO: 7)
IL1b-5' 5'-GGAGAGTGTGGATCCCAAGCIIIIICCAAAGAAG-3';
and (SEQ ID NO: 8)
IL1b-3' 5'-AGACCTCAGTGCAGGCTATGIIIIITTCATCCC-3'.
```

The DS primers for IL-10 used in the Example (600 bp) are:

```
                                        (SEQ ID NO: 37)
IL10-5' 5'-AAGGCCATGAATGAATTTGAIIIIITCATCAACTG-3';
and (SEQ ID NO: 38)
IL10-3' 5'-TGACAGTAGGGGAACCCTCTIIIIIGCTGCAGG-3'.
```

A. Monoplex PCR Using One Set of Cytokine Family Gene-Specific DS Primers

The single target PCR amplification for each cytokine family gene was conducted in a final volume of 20 µl containing 2 µl (50 ng) of the mouse genomic DNA, 2 µl of 10×PCR reaction buffer containing 15 mM $MgCl_2$ (Roche), 2 µl of dNTP (2 mM each dATP, dCTP, dGTP, dTTP), 1 µl of each cytokine family gene-specific 5' DS primer (10 µM), 1 µl of each cytokine family gene-specific 3' DS primer (10 µM), and 0.5 µl of Taq polymerase (5 units/µl; Roche); the tube containing the reaction mixture was placed in a preheated (94° C.) thermal cycler; samples were denatured for 5 min at 94° C. and subjected to 30 cycles of 1 min at 94° C., 1 min at 60-65° C., and 1 min at 72° C., followed by a 7-min incubation at 72° C.

B. Multiplex PCR Using 9 Sets of Cytokine Family Gene-Specific DS Primers

The multiplex PCR amplification was conducted in a single tube by using 9 sets of cytokine family gene-specific DS primers; the reaction mixture was in the final volume of 50 µl containing 100 ng of mouse genomic DNA, 5 µl of 10×PCR reaction buffer containing 15 mM $MgCl_2$ (Roche), 5 µl of dNTP (2 mM each dATP, dCTP, dGTP and dTTP), 1 µl of each cytokine family gene-specific 5' DS primer (0.2-5 µM), 1 µl of each cytokine family gene-specific 3' DS primer (0.5-5 M), and 0.5 µl of Taq polymerase (5 units/µl; Roche); the tube containing the reaction mixture was placed in a preheated (94° C.) thermal cycler; the PCR conditions are one cycle of 94° C. for 5 min, 50° C. for 3 min, and 72° C. for 3 min; followed by 29 cycles of 94° C. for 40 s, 60° C. for 1 min, and 72° C. for 40 s, and a 5-min final extension cycle at 72° C.

Figure 9:
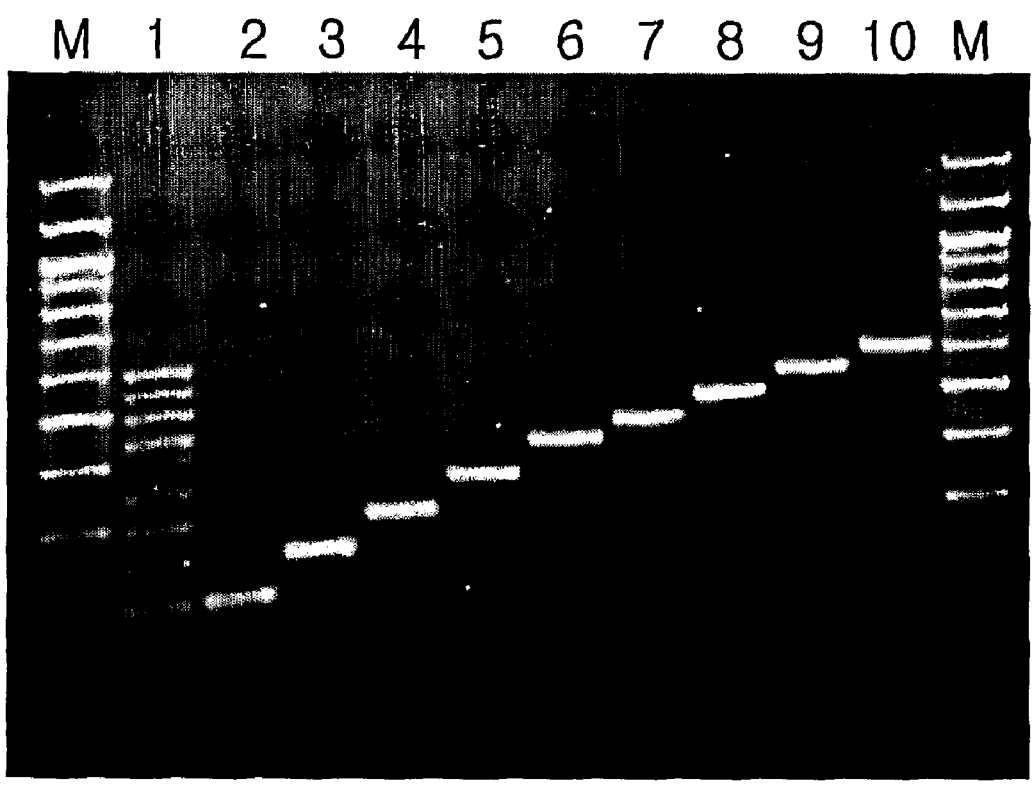
FIG. 9 shows the results of multiplex PCR using 9 sets of cytokine family gene-specific dual specificity primers. Lane 1, multiplex PCR for 9 cytokine genes; Lane 2, monoplex PCR for IL-3 (200 bp); Lane 3, monoplex PCR for IL-15 (250 bp); Lane 4, monoplex PCR for IL-18 (300 bp); Lane 5, monoplex PCR for IL-25 (350 bp); Lane 6, monoplex PCR for IL-2 (400 bp); Lane 7, monoplex PCR for IL-6 (450 bp); Lane 8, monoplex PCR for IL-19 (500 bp); Lane 9, monoplex PCR for IL-1β (550 bp); and Lane 10, monoplex PCR for EL-10 (600 bp). M is a 100-bp size marker generated by Forever 100-bp Ladder Personalizer.

As shown in FIG. 9, multiplex PCR amplification generates multiple bands which correspond to the expected sizes from 200 bp to 600 bp for 9 different cytokine gene products (FIG. 4, lane 1). Each monoplex PCR amplification generated a single band which corresponds to the expected size of 200 bp for IL-3 (FIG. 4, lane 2), 250 bp for IL-15 (FIG. 4, lane 3), 300 bp for IL-18 (FIG. 4, lane 4), 350 bp for IL-25 (FIG. 4, lane 5), 400 bp for IL-2 (FIG. 4, lane 6), 450 bp for IL-6 (FIG. 4, lane 7), 500 bp for IL-19 (FIG. 4, lane 8), 550 bp for IL-1beta (FIG. 4, lane 9), and 600 bp for IL-10 (FIG. 4, lane 10), respectively.

Accordingly, it could be appreciated that the DS primers developed by the present invention can be successfully applied to multiplex PCR. The unique structure of DS oligonucleotides allows to overcome the common problem of any conventional multiplex PCR, namely primer interference and dimmer formation.

Example 6

Detection of Human Metapneumovirus Using Mismatch Tolerance of Dual Specificity (DS) Oligonucleotides To demonstrate the application of DS oligonucleotide primers in mismatch tolerance, DS primers were applied to detect human metapnemovirus (hMPV) in clinical samples. The process and results for the detection of human metapnemovirus using DS primers are described herein. This Example should not be construed as limiting the applications of the invention to the detection of the specific virus.

The DS primers were designed based on the conserved region of the fusion glycoprotein (F) gene generated by aligning sequences of all available hMPV isolates (see Table 1). To tolerate the genetic diversity of these isolates, the primers were designed based on the following criteria: (a) conserved regions should be at least 30 nucleotides in length despite the presence of one or more, yet limited, base pair mismatches (Table 1); (b) most mismatched sequences within the conserved regions are preferably located in the separation portion in the DS primer (e.g., hMPV 5'-585, hMPV 3'-698, and hMPV 3'-1007); (c) otherwise, the mismatched nucleotides are located in the 5'-end portion, some of which could be replaced with universal bases such as deoxyinosines (e.g., hMPV 3'-698 and hMPV 3'-1007); and (d) one or two mismatched nucleotide(s) in the 3'-end portion can be replaced with degenerate nucleotide(s) or universal base(s) (e.g., hMPV 3'-1007).

The target PCR amplification of hMPV F gene was conducted in a final volume of 20 μl containing 2 μl (30 ng) of the first strand cDNA, 2 μl of 10×PCR reaction buffer containing 15 mM $MgCl_2$ (Roche), 2 μl of dNTP (2 mM each dATP, dCTP, dGTP and dTTP), 1 μl of 5' hMPV-specific DS primer (hMPV 5'-585; 10 μM), 1 μl of 3' hMPV-specific DS primer (hMPV 3'-698 or hNPV 3'-1007; 10 μM), and 0.5 μl of Taq polymerase (5 units/μl; Roche); the tube containing the reaction mixture was placed in a preheated (94° C.) thermal cycler; samples were denatured for 5 min at 94° C. and subjected to 30 cycles of 1 min at 94° C., 1 min at 60-65° C., and 1 min at 72° C., followed by a 7-min incubation at 72° C.

Figure 10:
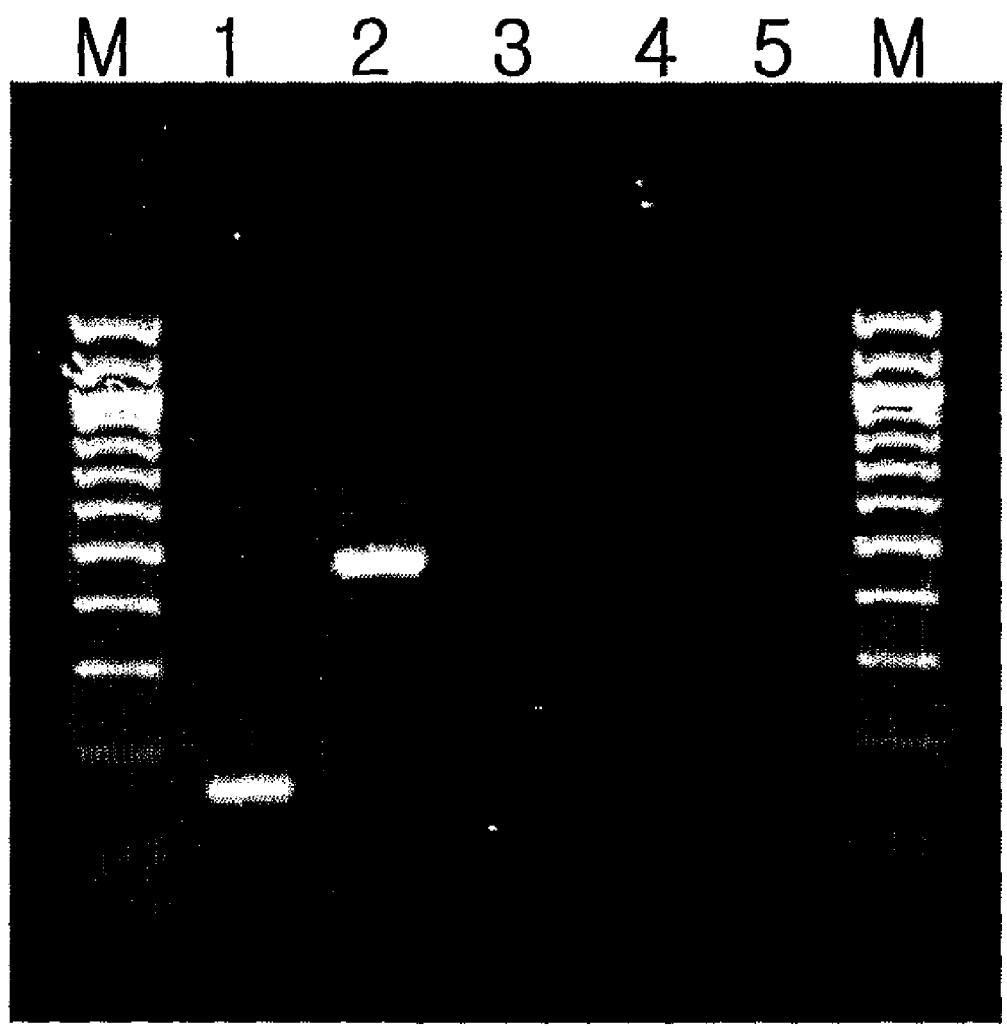
FIG. 10 shows the results of PCR amplifications of the fusion glycoprotein (F) gene of human metapneumovirus (hMPV) by use of the dual specificity oligonucleotide primers. Lane 1, target PCR using hMPV5'-585 and hMPV 3'-698 primer set; Lane 2, target PCR using hMPV5'-585 and hMPV 3'-1007 primer sets; Lane 3, target PCR using human β-actin primers; Lane 4, target PCR without template; and Lane 5, target PCR without template.

As shown in FIG. 10B, each pair of hMPV-specific DS primers (hMPV 5'-585 and hMPV 3'-698, and hMPV 5'-585 and hMPV 3'-1007) generates a single band which corresponds to the expected sizes of 150-bp and 459-bp, respectively (lanes 1 and 2). Subsequent sequence analysis of the

TABLE 1 hMIPV-Specific DS Oligonucleotide Primers Based on the
Conserved Region of the Fusion Glycoprotein (F) Gene of
All Available hMPV Isolates

| Primer | Sequence | No. of Isolates |
|---|---|---|
| Virus sequences | ......AGCTTCAGTCAATTCAACAGAAGGTTCCTAAATGTTG...... | 1 |
| | ......AGCTTCAGTCAATTCAACAGAAGATTTCTAAATGTTG...... | 3 |
| | ......AGCTTCAGTCAATTCAACAGAAGATTCCTAAATGTTG...... | 4 |
| | ......AGCTTCAGTCAATTCAACAGAAGATTTCTAAATGTTG...... | 1 |
| | ......AGCTTCAGTCAATTCAACAGAAGATTCCTAAATGTTG...... | 9 |
| | ......AGCTTCAGTCAATTCAACAGAAGGTTTCTAAATGTTG...... | 14 |
| 5'-primer (585): | 5'-AGCTTCAGTCAATTCAACAGAAIIIICTAAATGTTG3' | |
| Virus sequences | ......AACATCAGTTTTATTTGTCCTGCAGATGTTGGCATGT...... | 4 |
| | ......AACATCAGTTTTATCTGCCCTGCAGATGTTGGCATGT...... | 3 |
| | ......AACATTAGTTTTATCTCTCCTGCAGATGTTGGCATGT...... | 12 |
| | ......AACATCAGTTTTATCTGTCCTGCAGATGTTGGCATGT...... | 2 |
| | ......AACATCAATTTTATTTGTCCTGCAGATGTTGGCATGT...... | 3 |
| | ......AACATCAATTTTATTTGTCCTGCAGATGTTGGCATGT...... | 3 |
| | ......AACATCAATTTTATTTGTCCTGCAGATGTTGGCATGT...... | 5 |
| 3'-Primer (698): | 5'-AACATCAITTTTATITGTCCTGCAIIIIITGGCATGT-3' | |
| Virus sequences | ......TTGACTGCTCAGCAACATTGATTCCTGCTGCTGTGTC...... | 2 |
| | ......TTGATTGCTCAGCAACATTGATCCCTGCTGCTGTGTC...... | 7 |
| | ......TTGATTGCTCAGCAACATTGATCCCTGCA**GCTGTGTC...... | 8 |
| | ......TTGATTGCTCAGCGACATTGATCCCTGCTGCTGTGTC...... | 1 |
| | ......TTGATTGTTCAGCAACATTGATCCCTGCTGCTGTGTC...... | 1 |
| | ......TTGATTGCTCAGCAACATTAATTCCTGCTGCTGTGTC...... | 9 |
| | ......TTGATTGCTCAGCAACATTAATTCCCGCTGCTGTGTC...... | 2 |
| 3'-Primer (1007): | 5'-TTGAITGCTCAGCIACATTGATIIIII**CWGCTGTGTC3' | |

* Genetic diversity between hMPV isolates is shown as underlined nucleotides.

The DS primers specific to hMPV F gene used in the Example are: hMPV 5'-585 5'-AGCTTCAGTCAATTCAA-CAGAAIIIIICTAAATGTTG-3' (SEQ ID NO:39);

hMPV 3'-698 5'-AACATCAITTTTATITGTCCTGCAII-IIITGGCATGT-3' (SEQ ID NO:40); and hMPV 3'-1007 5'-TTGAITGCTCAGCIACATTGATII-IIICWGCTGTGTC-3' (SEQ ID NO:41), wherein W can be A or T, and I is deoxyinosine.

Viral total RNA was extracted by using the RNAzol B method according to the manufacturer's protocol (RNAzol LS; Tel-Test, Inc.). Reverse transcription reaction was performed to synthesize cDNA using the viral RNA for 1.5 hr at 42° C. in a reaction volume of 20 μl composed of the following: 5 μl of total RNA (approximately 100 ng), 4 μl of 5× reaction buffer (Invitrogen, USA), 5 μl of dNTPs (each 5 mM), 2 μl of 10 μM random hexadeoxynucleotides, 0.5 μl of RNase inhibitor (40 units/μl, Promega), and 1 μl of Moloney murine leukemia virus reverse transcriptase (200 units/μl, Promega).

products confirmed that they are the partial sequences of the hMPV fusion glycoprotein (F) gene. In contrast, these primers generate no product in a negative control PCR without the template (lanes 4 and 5). As a positive control, human beta-actin-specific primer set was used (lane 3).

These results indicate that the DS primers can be applied to detect hMPVs from patient with respiratory infections. Thus, it could be realized that the DS oligonucleotides can be adapted, as primers in PCR amplification or probes in oligonucleotide chip, to all potential situations encountered in the field.

Example 7

Detection of Target Nucleotide Sequence Using DS Oligo-Immobilized Microarray

The DS oligos complementary to a region of a target nucleic acid molecule are synthesized by means of a DNA synthesizer (Expedite 8900 Nucleic Acid Synthesis System, Applied Biosystems (ABI)) according to a standard protocol. The synthesized DS oligos are immobilized on a glass slide for microarray. Then, a template-dependent extension reaction mixture containing 50-200 ng of DNA sample, 5 µl of 10×PCR reaction buffer (Promega), 5 µl of 15 mM MgCl$_2$, 5 µl of fluorescence-labeled dNTP (2 mM each dATP, dCTP, dGTP and dTTP) and 0.5 µl of Taq polymerase (5 units/µl; Promega) is added to the microarray, after which the microarray is placed in a preheated (94° C.) thermal cycler. The template-dependent extension reaction is conducted according to the following thermal cycle: denaturation for 5 min at 94° C., and 15-50 cycles of 1 min at 94° C., 1-3 min at 50-65° C. and 1-4 min at 60-72° C., followed by a 5-min extension at 72° C. Following the template-dependent extension reaction, the extended DS oligos are washed and detected by its fluorescent images through a microarray scanner, followed by analysis of the images.

Example 8

SNP (Single Nucleotide Polymorphism) Genotyping Using DS Oligonucleotides

The DS oligos are synthesized by means of a DNA synthesizer (Expedite 8900 Nucleic Acid Synthesis System, Applied Biosystems (ABI)) according to a standard protocol with placing a polymorphic base (interrogation site) in the center of 3'-low $T_m$ specificity portion. The synthesized oligonucleotides are immobilized on a glass slide for microarray. Then, a template-dependent extension reaction mixture containing 50-200 ng of DNA sample, 5 µl of 10×PCR reaction buffer (Promega), 5 µl of 15 mM MgCl$_2$, 5 µl of fluorescence-labeled dNTP (2 mM each dATP, dCTP, dGTP and dTTP) and 0.5 µl of Taq polymerase (5 units/µl; Promega) is added to the microarray, after which the microarray is placed in a preheated (94° C.) thermal cycler. The template-dependent extension reaction is conducted according to the following thermal cycle: denaturation for 5 min at 94° C., and 15-50 cycles of 1 min at 94° C., 1-3 min at 50-65° C. and 1-4 min at 60-72° C., followed by a 5-min extension at 72° C. Following the template-dependent extension reaction, the extended DS oligos are washed and detected by its fluorescent images through a microarray scanner, followed by analysis of the images.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for synthesizing a nucleic acid molecule using a dual specificity oligonucleotide by a template-dependent extension reaction, comprising:
    (a) annealing the dual specificity oligonucleotide to a template nucleic acid molecule, wherein the dual specificity oligonucleotide is represented by the formula: 5'-$X_p$-$Y_q$-$Z_r$-3', wherein,
        $X_p$ is a 5'-high $T_m$ specificity portion having a hybridizing nucleotide sequence substantially complementary to a site on the template nucleic acid molecule to hybridize therewith,
        $Y_q$ is a separation portion comprising at least three contiguous universal bases,
        $Z_r$ is a 3'-low $T_m$ specificity portion having a hybridizing nucleotide sequence substantially complementary to a site on the template nucleic acid molecule to hybridize therewith,
        p, q and r are the number of nucleotides,
        p is an integer of at least 15,
        q is an integer of at least 3,
        r is an integer of at least 4, and
        X, Y, and Z are deoxyribonucleotide or ribonucleotide;
    wherein the $T_m$ of the 5'-high $T_m$ specificity portion is at least 20° C. higher than that of the 3'-low $T_m$ specificity portion;
    wherein the separation portion has the lowest $T_m$ in the three portions;
    wherein the 5'-high $T_m$ specificity portion is longer than the 3'-low $T_m$ specificity portion;
    wherein the separation portion forms a non base-pairing that does not serve as a hybridizing site and does not interact with the template nucleic acid molecule for base pairing under conditions that the 5'-high $T_m$ specificity portion and the 3'-low $T_m$ specificity portion are annealed to the template nucleic acid molecule, enabling the 5'-high $T_m$ specificity portion to separate from the 3'-low $T_m$ specificity portion in terms of annealing specificity to the template nucleic acid molecule, whereby the annealing specificity of the dual specificity oligonucleotide is determined dually by the 5'-high $T_m$ specificity portion and the 3'-low $T_m$ specificity portion such that the overall annealing specificity of the dual specificity oligonucleotide is enhanced;
    wherein the annealing is performed under conditions that annealing solely by the 3'-low $T_m$ specificity portion does not occur; and
    wherein 5'-high $T_m$ specificity portion and the 3'-low $T_m$ specificity portion of the dual specificity oligonucleotide is initially annealed to the template nucleic acid molecule; and
    (b) extending the dual specificity oligonucleotide to synthesize the nucleic acid molecule complementary to the template nucleic acid.

2. A method for selectively amplifying a target nucleic acid sequence from a DNA or a mixture of nucleic acids, comprising:
    amplifying the target nucleic acid sequence by performing at least two cycles of primer annealing, primer extending and denaturing using a primer set
    said primer set comprising at least one dual specificity oligonucleotide with enhanced annealing specificity;
    wherein the dual specificity oligonucleotide is represented by the formula: 5'-$X_p$-$Y_q$-$Z_r$-3', wherein,
        $X_p$ is a 5'-high $T_m$ specificity portion having a hybridizing nucleotide sequence substantially complementary to a site on the target nucleic acid sequence to hybridize therewith,
        $Y_q$ is a separation portion comprising at least three contiguous universal bases,
        $Z_r$ is a 3'-low $T_m$ specificity portion having a hybridizing nucleotide sequence substantially complementary to a site on the target nucleic acid sequence to hybridize therewith,
        p, q and r are the number of nucleotides,
        p is an integer of at least 15,
        q is an integer of at least 3,
        r is an integer of at least 4, and
        X, Y, and Z are deoxyribonucleotide or ribonucleotide;

wherein the $T_m$ of the 5'-high $T_m$ specificity portion is at least 20° C. higher than that of the 3'-low $T_m$ specificity portion;

wherein the separation portion has the lowest $T_m$ in the three portions;

wherein the 5'-high $T_m$ specificity is longer than the 3'-low specificity portion;

wherein the separation portion forms a non base-pairing that does not serve as a hybridizing site and does not interact with the target nucleic acid sequence for base pairing, under conditions that the 5'-high $T_m$ specificity portion and the 3'-low $T_m$ specificity portion are annealed to the target nucleic acid sequence enabling the 5'-high $T_m$ specificity portion to separate from the 3'-low $T_m$ specificity portion in terms of annealing specificity to the target nucleic acid sequence, whereby the annealing specificity of the dual specificity oligonucleotide is determined dually by the 5'-high $T_m$ specificity portion and the 3'-low $T_m$ specificity portion such that the overall annealing specificity of the dual specificity oligonucleotide is enhanced;

wherein annealing in the amplification reaction is performed under conditions that annealing solely by the 3'-low $T_m$ specificity portion does not occur; and wherein a first cycle and a second cycle of the amplification reaction involve annealing of both the 5'-high $T_m$ specificity portion and the 3'-low $T_m$ specificity portion of the dual specificity oligonucleotide to the target nucleic acid sequence.

3. A method for amplifying two or more target nucleotide sequences simultaneously using two or more pairs of primers in the same reaction, comprising:

amplifying the target nucleotide sequences by performing at least two cycles of primer annealing, primer extending and denaturing, using two or more primer pairs in which at least one primer of the primer pair is a dual specificity oligonucleotide, characterized in that the dual specificity oligonucleotide is represented by the formula: 5'-$X_p$-$Y_q$-$Z_r$-3', wherein, $X_p$ is a 5'-high $T_m$ specificity portion having a hybridizing nucleotide sequence substantially complementary to a site on the target nucleic acid sequence to hybridize therewith, $Y_q$ is a separation portion comprising at least three contiguous universal bases, $Z_r$ is a 3'-low $T_m$ specificity portion having a hybridizing nucleotide sequence substantially complementary to a site on the target nucleic acid sequence to hybridize therewith, p, q and r are the number of nucleotides, p is an integer of at least 15, \ q is an integer of at least 3, r is an integer of at least 4, and

X, Y, and Z are deoxyribonucleotide or ribonucleotide;

wherein the $T_m$ of the 5'-high $T_m$ specificity portion is at least 20° C. higher than that of the 3'-low $T_m$ specificity portion;

wherein the separation portion has the lowest $T_m$ in the three portions;

wherein the 5'-high $T_m$ specificity portion is longer than the 3'-low $T_m$ specificity portion;

wherein the separation portion forms a non base-pairing that does not serve as a hybridizing site and does not interact with the target nucleic acid sequence for base pairing, under conditions that the 5'-high $T_m$ specificity portion and the 3'-low $T_m$ specificity portion are annealed to the target nucleic acid sequence, enabling the 5'-high $T_m$ specificity portion to separate from the 3'-low $T_m$ specificity portion in terms of annealing specificity to the target nucleic acid sequence, whereby the annealing specificity of the dual specificity oligonucleotide is determined dually by the 5'-high $T_m$ specificity portion and the 3'-low $T_m$ specificity portion such that the overall annealing specificity of the dual specificity oligonucleotide is enhanced;

wherein annealing in the amplification reaction is performed under conditions that annealing solely by the 3'-low $T_m$ specificity portion does not occur; and wherein a first cycle and a second cycle of the amplification reaction involve annealing of both the 5'-high $T_m$ specificity portion and the 3'-low $T_m$ specificity portion of the dual specificity oligonucleotide to the target nucleotide sequences.

4. A method for sequencing a target nucleic acid molecule using a dual specificity oligonucleotide from a DNA or a mixture of nucleic acids, comprising:

(a) synthesizing a complementary nucleic acid molecule to the target nucleic acid molecule to be sequenced by performing at least two cycles of primer annealing, primer extending and denaturing, using the dual specificity oligonucleotide as a sequencing primer; wherein the dual specificity oligonucleotide is represented by the following general formula: 5'-$X_p$-$Y_q$-$Z_r$-3', wherein, $X_p$ is a 5'-high $T_m$ specificity portion having a hybridizing nucleotide sequence substantially complementary to a site on the target nucleic acid sequence to hybridize therewith, $Y_q$ is a separation portion comprising at least three contiguous universal bases, $Z_r$ is a 3'-low $T_m$ specificity portion having a hybridizing nucleotide sequence substantially complementary to a site on the target nucleic acid sequence to hybridize therewith, p, q and r are the number of nucleotides, p is an integer of at least 15, q is an integer of at least 3, r is an integer of at least 4; and X, Y, and Z are deoxyribonucleotide or ribonucleotide;

wherein the $T_m$ of the 5'-high $T_m$ specificity portion is at least 20° C. higher than that of the 3'-low $T_m$ specificity portion;

wherein the separation portion has the lowest $T_m$ in the three portions;

wherein the 5'-high $T_m$ specificity portion is longer than the 3'-low $T_m$ specificity portion;

wherein the separation portion forms a non base-pairing that does not serve as a hybridizing site and not interact with the target nucleic acid sequence for base pairing, under conditions that the 5'-high $T_m$ specificity portion and the 3'-low $T_m$ specificity portion are annealed to the target nucleic acid sequence, enabling the 5'-high $T_m$ to separate from the 3'-low $T_m$ specificity portion in terms of annealing specificity to the target nucleic acid sequence, whereby the annealing specificity of the dual specificity oligonucleotide is determined dually by the 5'-high $T_m$ specificity portion and the 3'-low $T_m$ specificity portion such that the overall annealing specificity of the dual specificity oligonucleotide is enhanced;

wherein annealing in the reaction is performed under conditions that annealing solely by the 3'-low $T_m$ specificity portion does not occur;

wherein both the 5'-high $T_m$ specificity portion and the 3'-low $T_m$ specificity portion of the dual specificity oligonucleotide is initially annealed to the target nucleic acid molecule; and (b) determining a nucleotide sequence of the synthesized complementary nucleic acid molecule.

5. A method for detecting a nucleic acid molecule with genetic diversity by a template-dependent extension reaction of a dual specificity oligonucleotide, comprising:

(a) synthesizing a complementary nucleic acid molecule to the target nucleic acid molecule to be sequenced by performing at least two cycles of primer annealing, primer extending and denaturing, using the dual specificity oligonucleotide as a sequencing primer; wherein the dual specificity oligonucleotide is represented by the following general formula: 5'-$X_p$—$Y_q$-$Z_r$-3', wherein, $X_p$ is a 5'-high $T_m$ specificity portion having a hybridizing nucleotide sequence substantially complementary to a site on the target nucleic acid sequence to hybridize therewith, $Y_q$ is a separation portion comprising at least three contiguous universal bases, $Z_r$ is a 3'-low $T_m$ specificity portion having a hybridizing nucleotide sequence substantially complementary to a site on the target nucleic acid sequence to hybridize therewith, p, q and r are the number of nucleotides,
p is an integer of at least 15,
q is an integer of at least 3,
r is an integer of at least 4; and
X, Y, and Z are deoxyribonucleotide or ribonucleotide;

wherein the $T_m$ of the 5'-high $T_m$ specificity portion is at least 20° C. higher than that of the 3'-low $T_m$ specificity portion;

wherein the separation portion has the lowest $T_m$ in the three portions;

wherein the 5'-high $T_m$ specificity portion is longer than the 3'-low $T_m$ specificity portion;

wherein the separation portion forms a non base pairing that does not serve as a hybridizing site and not interact with the target nucleic acid sequence for base pairing, under conditions that the 5'-high $T_m$ specificity and the 3'-low $T_m$ specificity portion are annealed to the target nucleic acid sequence, enabling the 5'-high $T_m$ to separate from the 3'-low $T_m$ specificity portion in terms of annealing specificity to the target nucleic acid sequence, whereby the annealing specificity of the dual specificity oligonucleotide is determined dually by the 5'-high $T_m$ specificity portion and the 3'-low $T_m$ specificity portion such that the overall annealing specificity of the dual specificity oligonucleotide is enhanced;

wherein annealing in the reaction is performed under conditions that annealing solely by the 3'-low $T_m$ specificity portion does not occur; and wherein both the 5'-high $T_m$ specificity portion and the 3'-low $T_m$ specificity portion of the dual specificity oligonucleotide is initially annealed to the target nucleic acid molecule;

(b) extending the dual specificity oligonucleotide to synthesize the nucleic acid molecule complementary to the template; and (c) detecting the occurrence of the template-dependent extension of the dual specificity oligonucleotide.

6. A method for detecting a target nucleotide sequence in a nucleic acid sample by a template-dependent extension reaction of a dual specificity oligonucleotide, comprising:

(a) synthesizing a complementary nucleic acid molecule to the target nucleic acid molecule to be sequenced by performing at least two cycles of primer annealing, primer extending and denaturing, using the dual specificity oligonucleotide as a sequencing primer; wherein the dual specificity oligonucleotide is represented by the following general formula: 5'-$X_p$—$Y_q$-$Z_r$-3' wherein, $X_p$ is a 5'-high $T_m$ specificity portion having a hybridizing nucleotide sequence substantially complementary to a site on the target nucleic acid sequence to hybridize therewith, $Y_q$ is a separation portion comprising at least three contiguous universal bases, $Z_r$ is a 3'-low $T_m$ specificity portion having a hybridizing nucleotide sequence substantially complementary to a site on the target nucleic acid sequence to hybridize therewith, p, q and r are the number of nucleotides,
p is an integer of at least 15,
q is an integer of at least 3,
r is an integer of at least 4; and
X, Y, and Z are deoxyribonucleotide or ribonucleotide;

wherein the $T_m$ of the 5'-high $T_m$ specificity portion is at least 20° C. higher than that of the 3'-low $T_m$ specificity portion;

wherein the separation portion has the lowest $T_m$ in the three portions; wherein the 5'-high $T_m$ specificity portion is longer than the 3'-low $T_m$ specificity portion;

wherein the separation portion forms a non base-pairing that does not serve as a hybridizing site and not interact with the target nucleic acid sequence for base pairing, under conditions that the 5'-high $T_m$ specificity portion and the 3'-low $T_m$ specificity portion are annealed to the target nucleic acid sequence, enabling the 5'-high $T_m$ specificity portion to separate from the 3'-low $T_m$ specificity portion in terms of annealing specificity to the target nucleic acid sequence, whereby the annealing specificity of the dual specificity oligonucleotide is determined dually by the 5'-high $T_m$ specificity portion and the 3'-low $T_m$ specificity portion such that the overall annealing specificity of the dual specificity oligonucleotide is enhanced;

wherein annealing in the reaction is performed under conditions that annealing solely by the 3'-low $T_m$ specificity portion does not occur;

wherein 5'-high $T_m$ specificity portion and the 3'-low $T_m$ specificity portion of the dual specificity oligonucleotide is initially annealed to the target nucleic acid molecule; and (b) analyzing the occurrence of the template-dependent extension.

7. The method according to any one of claim 1-6, wherein the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof.

8. The method according to claim 7, wherein the universal base is deoxyinosine, 1-(2'-deoxy-beta-D-ribofuranosyl)-3-nitropyrrole or 5-nitroindole.

9. The method according to claim 8, wherein the universal base is deoxyinosine.

10. The method according to any one of claim 1-6, wherein the 3'-low $T_m$ specificity portion has the hybridizing nucleotide sequence perfectly complementary to the site on the template nucleic acid to hybridize therewith.

11. The method according to any one of claim 1-6, wherein the 5'-high $T_m$ specificity portion is 15 to 40 nucleotides in length.

12. The method according to claim 11, wherein the 5'-high $T_m$ specificity portion is 15 to 25 nucleotides in length.

13. The method according to any one of claim 1-6, wherein the separation portion is 3 to 10 nucleotides in length.

14. The method according to any one of claim 1-6, wherein the 3'-low $T_m$ specificity portion is a 4 to 15 nucleotides in length.

15. The method according to any one of claim 1-6, wherein the 5'-high $T_m$ specificity portion is 15 to 25 nucleotides in length, the separation portion is 3 to 10 nucleotides in length, and the 3'-low $T_m$ specificity portion is 4 to 15 nucleotides in length.

16. The method according to any one of claim 1-6, wherein the $T_m$ of the 5'-high $T_m$ specificity portion ranges from 40° C. to 80° C.

17. The method according to any one of claim 1-6, wherein the $T_m$ of the 3'-low $T_m$ specificity portion ranges from 10° C. to 40° C.

18. The method according to any one of claim 1-6, wherein the $T_m$ of the separation portion ranges from 3° C. to 15° C.

19. The method according to any one of claims 1-6, wherein the annealing is performed at temperature ranging from 45° C. to 68° C.

20. The method according to claim 1 or 5, wherein the synthesis of a target nucleic acid sequence is achieved by repeating the process of the template-dependent extension reaction in which the dual specificity oligonucleotide annealing and extension steps are followed by denaturation step.

21. The method according to claim 2 or 3, wherein the amplification is performed in accordance with polymerase chain reaction.

22. The method according to claim 4, wherein the target nucleic acid molecule to be sequenced is contained in a genomic DNA or a population of cDNAs.

23. The method according to claim 5, wherein the nucleic acid molecule with genetic diversity is a nucleic acid of a virus exhibiting genetic diversity.

24. A method for enabling an annealing specificity of an oligonucleotide to be dually determined through a structure of the oligonucleotide, comprising:
  (a) selecting a target nucleic acid sequence;
  (b) designing a sequence of an oligonucleotide having (i) a hybridizing sequence substantially complementary to the target nucleic acid and (ii) a separation portion comprising at least three contiguous universal bases, such that the separation portion intervenes in the hybridizing sequence to form three portions in the oligonucleotide; and
  (c) determining the position of the separation portion in the oligonucleotide to allow a portion at the 5'-direction of the separation portion to have a higher $T_m$ than a portion at the 3'-direction of the separation portion and to allow the separation portion to have the lowest $T_m$ in the three portions, thereby providing an oligonucleotide having three distinct portions with different $T_m$ values from one another in which (i) a 5'-high $T_m$ specificity portion of the oligonucleotide has a hybridizing nucleotide sequence substantially complementary to the target nucleic acid and is at least 15 nucleotides in length, (ii) a 3'-low $T_m$ specificity portion of the oligonucleotide has a hybridizing nucleotide sequence substantially complementary to the target nucleic acid and is at least 4 nucleotides in length; and (iii) the separation portion of the oligonucleotide between the 5'-high $T_m$ specificity portion and 3'-low $T_m$ specificity portion comprises at least three contiguous universal bases; and the $T_m$ of the 5'-high $T_m$ specificity portion is higher at least 20° C. than that of the 3'-low $T_m$ specificity portion and the separation portion has the lowest $T_m$ in the three portions; the 5'-high $T_m$ specificity portion is longer than the 3'-low $T_m$ specificity portion; wherein the oligonucleotide is initially annealed to the target nucleic acid in amplification or hybridization reactions, whereby the annealing specificity of the oligonucleotide to the target nucleic acid is determined dually by both the 5'-high $T_m$ specificity portion and the 3'-low $T_m$ specificity portion.

25. The method according to claim 24, wherein the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof.

26. The method according to claim 25, wherein the universal base is deoxyinosine, 1-(2'-deoxy-beta-D-ribofuranosyl)-3-nitropyrrole or 5-nitroindole.

27. The method according to claim 26, wherein the universal base is deoxyinosine.

28. The method according to claim 24, wherein the 3'-low $T_m$ specificity portion has the hybridizing nucleotide sequence perfectly complementary to the site on the template nucleic acid to hybridize therewith.

29. The method according to claim 24, wherein the 5'-high $T_m$ specificity portion is 15 to 40 nucleotides in length.

30. The method according to claim 29, wherein the 5'-high $T_m$ specificity portion is 15 to 25 nucleotides in length.

31. The method according to claim 24, wherein the separation portion is 3 to 10 nucleotides in length.

32. The method according to claim 24, wherein the 3'-low $T_m$ specificity portion is 4 to 15 nucleotides in length.

33. The method according to claim 24, wherein the 5'-high $T_m$ specificity portion is 15 to 25 nucleotides in length, the separation portion is 3 to 10 nucleotides in length and the 3'-low $T_m$ specificity portion is 4 to 15 nucleotides in length.

34. The method according to claim 24, wherein the $T_m$ of the 5'-high $T_m$ specificity portion ranges from 40° C. to 80° C.

35. The method according to claim 24, wherein the $T_m$ of the 3'-low $T_m$ specificity portion ranges from 10° C. to 40° C.

36. The method according to claim 24, wherein the $T_m$ of the separation portion ranges from 3° C. to 15° C.

* * * * *